US008608840B2

(12) United States Patent
Hopper et al.

(10) Patent No.: US 8,608,840 B2
(45) Date of Patent: Dec. 17, 2013

(54) CHOKE ASSEMBLY

(71) Applicant: Cameron International Corporation, Houston, TX (US)

(72) Inventors: Hans Paul Hopper, Aberdeen (GB); Derek Meek, Aberdeen (GB)

(73) Assignee: Cameron International Corporation, Houston, TX (US)

( * ) Notice: Subject to any disclaimer, the term of this patent is extended or adjusted under 35 U.S.C. 154(b) by 0 days.

(21) Appl. No.: 13/895,689

(22) Filed: May 16, 2013

(65) Prior Publication Data

US 2013/0256216 A1   Oct. 3, 2013

Related U.S. Application Data

(63) Continuation of application No. 12/680,038, filed as application No. PCT/GB2008/003321 on Sep. 24, 2008, now Pat. No. 8,460,438.

(30) Foreign Application Priority Data

Sep. 26, 2007 (EP) .................................... 07253806

(51) Int. Cl.
*B01D 19/00* (2006.01)
(52) U.S. Cl.
USPC ................... 96/209; 96/213; 96/212; 96/211; 96/188; 96/261; 96/243
(58) Field of Classification Search
USPC .............. 95/261, 260, 243; 96/209, 213, 212, 96/204, 211, 188
See application file for complete search history.

(56) References Cited

U.S. PATENT DOCUMENTS

| 1,775,362 | A | * | 9/1930 | De Marcus | 96/165 |
|---|---|---|---|---|---|
| 2,765,045 | A | * | 10/1956 | Meyers | 95/176 |
| 5,824,212 | A | * | 10/1998 | Brockhoff | 210/194 |
| 5,880,378 | A | * | 3/1999 | Behring, II | 73/861.53 |
| 6,730,236 | B2 | * | 5/2004 | Kouba | 210/806 |
| 8,460,438 | B2 | * | 6/2013 | Meek et al. | 95/243 |
| 2005/0247203 | A1 | * | 11/2005 | Chevallet et al. | 96/209 |
| 2010/0242736 | A1 | * | 9/2010 | Herring et al. | 96/174 |
| 2010/0288389 | A1 | * | 11/2010 | Hopper et al. | 138/43 |

FOREIGN PATENT DOCUMENTS

DE            4407835 A1 *  9/1995

\* cited by examiner

*Primary Examiner* — Duane Smith
*Assistant Examiner* — Douglas Theisen
(74) *Attorney, Agent, or Firm* — Chamberlain Hrdlicka

(57) ABSTRACT

A choke assembly comprises an inlet (48) for a multiphase fluid stream, the stream comprising a first relatively heavy fluid phase and a second relatively light fluid phase; a first fluid outlet (116); a choke element (22) disposed between the inlet and the first fluid outlet operable to control the flow of fluid between the inlet and the first fluid outlet; a separation chamber (40, 114) disposed to provide separation of phases in the fluid stream upstream of the choke element; and a second outlet (118) for removing fluid from the separation cavity. The choke assembly is of particular use in the control of fluid streams produced from a subterranean well, in particular oil and gas produced from a subsea well.

20 Claims, 15 Drawing Sheets

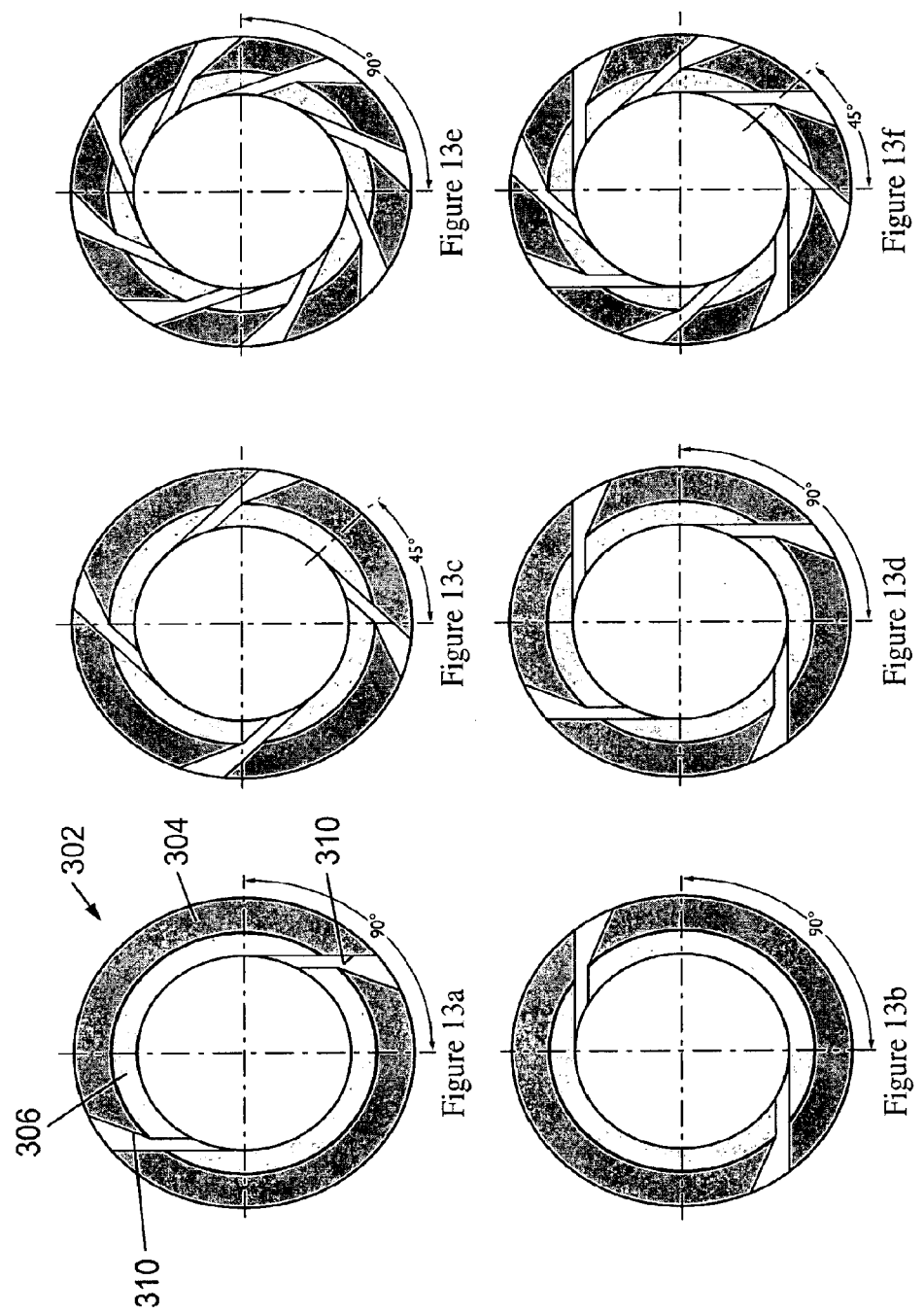

CHOKE ASSEMBLY

This application is a continuation of and claims benefit to U.S. patent application Ser. No. 12/680,038, filed on 30 Apr. 2010, now U.S. Pat. No. 8,460,438, entitled "CHOKE ASSEMBLY".

STATEMENT REGARDING FEDERALLY SPONSORED RESEARCH OR DEVELOPMENT

Not applicable.

BACKGROUND

The present invention relates to a choke assembly for controlling the flowrate or pressure of a fluid. The invention relates in particular to a choke assembly for use in the control of flow of oil and/or gas streams, especially in the control of fluid streams produced from subterranean wells. The choke assembly of the present invention is particularly suitable for use in subsea installations for the drilling of subterranean wells and/or the subsea production of oil and gas.

The flowrate and/or pressure of a fluid stream are generally controlled in use by some form of valve assembly, in which the size of the orifice or conduit through which the fluid is caused to pass is altered. A particular form of assembly commonly employed for the control of fluid flowrate and/or pressure is a choke assembly. Known choke assemblies comprise a conduit having a plurality of orifices and a means for progressively opening and closing some or all of the orifices to allow the passage of fluid therethrough. The desired pressure and/or flowrate is determined by the number and size of orifices that are open and available for the passage of fluid.

A common design of choke assembly is of the plug and cage variety. A generally cylindrical cage is disposed within the choke body, the cage being provided with a plurality of openings or orifices therethrough. A cylindrical plug is disposed to be moveable co-axially with respect to the cage, so as to open or close the orifices in the cage, depending upon the position of the plug. The orifices in the cage are disposed along the path of movement of the plug, such that movement of the plug from the fully closed to the fully open position along the longitudinal axis of the cage opens successive orifices, thereby increasing the cross-sectional area available for fluid to flow. Typically, the fluid to be controlled is introduced from the inlet of the choke assembly perpendicular to an annulus surrounding the exterior of the plug and cage, passes through the orifices of the cage into the interior of the cage and, from there to the outlet of the choke assembly. The orifices in the cage are disposed perpendicular to the longitudinal axis of the cage. Typically, equal and opposite orifices are used, to generate jets of fluid entering the interior of the cage to impinge on one another, thereby dissipating the energy in the fluid stream.

In general, known choke assemblies of the aforementioned type have one of two arrangements. In a first arrangement, the cage is fixed and the plug is moveable longitudinally with respect to the cage. The plug extends and is moveable within the cage. In a second arrangement, the cage is again fixed and the plug is moveable, but with the plug disposed externally to the cage (generally known as a sleeve). In general, the arrangement employing an external cage and an internal plug is preferred, as this provides a better degree of control of the fluid flowrate and/or pressure. However, there are several significant drawbacks with both designs of choke, in particular the design employing an external cage.

It is the case that a subterranean well produces a fluid stream having several phases of fluids. Liquid phases present in the fluid stream are typically oil and water. Water is being produced from subterranean wells in increasing quantities, for example as a result of operations to enhance oil recovery from a field by water injection. In addition, the fluid stream produced will typically contain significant volumes of gas.

Much effort is being put into developing systems to separate oil, water and gas from the fluid stream produced by wells. In particular, given the increasing depths at which subsea wellhead installations are operating, it is becoming increasingly desirable to avoid having to produce water from the well to the surface. Rather, there is increasing need to separate water produced from the well at the seabed, to allow for reinjection.

However, conventional choke assemblies provide an obstacle to achieving the desired fluid separation. The conventional plug/cage choke assembly has orifices extending perpendicularly through the cylindrical cage. The orifices are typically circular. As a result of this arrangement, the fluid passing through the choke assembly is subjected to very high rates of shear. This in turn generates significant mixing of the fluid phases, in some cases resulting in emulsification of the oil and water phases. This mixing significantly hinders the separation of the water, oil and gas phases.

Accordingly, there is a need for a choke assembly that provides the required level of fluid control, without subjecting the fluid stream to excessively high rates of shear.

U.S. Pat. No. 6,730,236 relates to a method for separating liquids in a separation system having a flow coalescing apparatus and a separation apparatus. The separation system includes a flow conditioning apparatus having an inlet and an outlet. A swirl chamber is disposed between the inlet and outlet and operates to create a swirling fluid flow pattern. It is suggested that this swirling pattern induces coalescence of liquid droplets in the fluid stream. The flow conditioning apparatus comprises an outer shell in which the fluid inlet is formed. The apparatus further comprises an inner swirl chamber having a helical pattern of tangential holes, whereby fluid enters the swirl chamber from the outer shell and is caused to flow in a helical pattern. The flow of fluid into the inner swirl chamber is controlled by a plunger assembly, including a conical head that is moveable longitudinally within the swirl chamber. Reciprocation of the conical head covers and uncovers holes in the helical pattern and allows the fluid flow to be controlled.

The flow conditioning system of U.S. Pat. No. 6,730,236 is intended for use in conjunction with a downstream apparatus for separating the fluid phases and acts to condition the flow by inducing coalescence of fluid bubbles and, if required, to act as a choke device to control the fluid flowrate. It would be advantageous of a system could be provided that combines the operation of a choke and a separation action. In addition, it would be particularly useful if such a system could act to separate solids from a fluid stream.

Further, the production of oil, water, and/or gas from a subterranean well, it is very often the case that the fluid stream has entrained therein significant quantities of solid material. The solid material, such as sand, silt and gravel, may be produced from the subterranean formations along with the oil and gas. Sand and gravel entrained with the oil and/or gas will enter the choke assembly together with the fluid stream. In addition, the well may produce quantities of metal particles that enter the choke, for example as a result of equipment wear or failure upstream of the choke assembly.

In the designs of choke discussed hereinbefore, the cage assembly is particularly vulnerable to damage from solids entrained with the fluid stream. Small particles entrained with the fluid generates a very high rate of wear on the cage and especially the plug, leading to poor control of the fluid flowrate and/or pressure and eventual failure of the choke. In addition, with the arrangement of perpendicularly extending, opposed orifices in the cage, solid particles and objects entrained with the fluid are directed onto the portion of the interior surface of the cage opposite the orifice. In extreme, but not uncommon cases, large solid particles impacting the cage assembly can destroy the cage. In all such cases, the inevitable result is that the choke assembly requires replacement. In the case of a subsea installation, perhaps at a depth of many thousands of feet of water, the replacement of a choke is a difficult, dangerous and time consuming task, during which production from the well may need to be shutdown. Chokes having the external cage/internal plug design are particularly vulnerable to damage and failure from entrained solids. Choke assemblies located close to the wellhead are particularly vulnerable to solids produced from the well. However, as such choke assemblies are typically operating at or close to wellhead pressure, their failure can lead to a potentially dangerous situation and their replacement is a particularly difficult task, especially at great depths of water.

Accordingly, there is a need for a choke assembly that reduces the damage caused to the cage of the choke assembly by solids entrained with the fluid being fed to the choke.

As noted, choke assemblies are required in order to reduce the pressure and/or flowrate of fluid streams, in particular fluid streams produced from subterranean wells. It has been found that this necessary choke operation can also be employed to provide a fluid separation function and to condition the fluid stream for further downstream processing. In particular, it has been found that the choking operation can be employed to separate solid particles entrained or suspended in fluid streams. Developments have also been made to the choke assembly to prevent such entrained and suspended solid particles from damaging the components of the choke, as hereinbefore described.

SUMMARY OF THE DISCLOSURE

According to a first aspect of the present invention, there is provided a choke assembly comprising:

an inlet for a multiphase fluid stream, the stream comprising a first relatively heavy fluid phase and a second relatively light fluid phase;

a first fluid outlet;

a choke element disposed between the inlet and the first fluid outlet operable to control the flow of fluid between the inlet and the first fluid outlet;

a separation chamber disposed to provide separation of phases in the fluid stream upstream of the choke element; and a second outlet for removing fluid from the separation cavity.

In the choke assembly, fluid enters through the inlet and flows towards the first or second outlet. Until separation of the fluid phases occurs in the separation chamber, the entire fluid stream will flow in the same direction. After separation, a portion of the fluid stream flows through the choke element to the first outlet, while the remaining portion of the fluid stream flows to the second outlet. References herein to 'upstream' and 'downstream' will be used to indicate the relative positions of features of the assembly and are to be construed in the light of this overall flow scheme.

The choke assembly of the first aspect of the present invention comprises a choke element disposed between a fluid inlet and a first fluid outlet. The choke element may be any arrangement that allows the flowrate and/or pressure of the fluid leaving through the first fluid outlet to be controlled. One suitable choke element arrangement is the plug and cage arrangement discussed hereinbefore, that is a perforated cage through which fluid may pass, with the flow of fluid through the cage being controlled by a moveable plug. Typically, the plug is moveable longitudinally within the cage. The plug may be disposed either upstream, that is outside, or downstream, that is inside, the cage, as required. A preferred arrangement has the plug disposed within the cage. Preferred choke elements employing the plug and cage arrangement are described hereinafter.

The choke assembly comprises a separation chamber disposed such that separation of the multiphase fluid stream occurs upstream of the choke element, such that all fluid passing through the choke element is caused first to flow through the separation chamber. A particularly preferred arrangement is one in which the choke element is disposed within the separation chamber, especially in which the choke element is arranged concentrically within the separation chamber and the separation chamber extends around the choke element.

The choke element is positioned in the assembly to receive a portion of the fluid after separation of the fluid phases has occurred in the separation chamber. The choke element is positioned to provide a flowpath for the lighter fluid factions, while allowing the heavier fluid fractions to remain within the separation chamber pass to the second outlet. Preferably, the choke element is disposed to receive fluid from a region of the separation chamber that is between the inlet and the second outlet. In this way, a portion of the fluid in the separation chamber is caused to pass through the choke element to the first outlet, while the remaining portion of the fluid bypasses the choke element and flows to the second outlet.

The inlet for the fluid is disposed so as to direct the fluid stream to be processed into the separation chamber. The inlet is preferably positioned to direct fluid into a region of the separation chamber that is displaced from the choke element, more particularly in a region of the separation chamber that is upstream of the choke element. In this way, separation of the fluid stream is allowed to occur prior to the fluid reaching and passing through the choke element.

The inlet may be of any suitable shape and orientation. In a preferred embodiment, the inlet is rectangular or square in cross-section. This preferred shape provides advantages with respect to the preferred arrangement and operation of the separation chamber using a rotational flow pattern for the fluid, as will be described hereinafter. The rectangular inlet may have any suitable aspect ratio, that is the ratio of the longest side to the shortest side. Preferably, the aspect ratio of the inlet is in the range of from 1:1 to 1:3.

The inlet may be oriented to direct the fluid into the separation chamber in any suitable manner. For example, the inlet may be positioned to direct incoming fluid radially into the separation chamber. Preferably, however, the inlet is oriented to direct the incoming into the separation at an angle to the radius of the separation, in order to generate a rotational flow pattern of the fluid in the separation chamber. Most preferably, the inlet is arranged at a tangent to the separation chamber, whereby incoming fluid is directed along a flowpath around the perimeter of the separation chamber.

The inlet may be oriented to direct fluid into the separation chamber perpendicular to the longitudinal axis of the separation chamber. However, it is preferred that the inlet is angled to direct fluid into the separation chamber at an angle to the normal to the longitudinal axis, such that the incoming fluid is directed into the separation chamber in a downstream direction. When the inlet is also arranged to direct the incoming fluid at an angle to the perpendicular to the longitudinal axis of the separation chamber, the fluid is caused to flow in a helical path in the downstream direction within the separation chamber. Most preferably, the inlet is angled such that the fluid rotating within the separation chamber is caused to avoid impacting the incoming fluid, that is pass the inlet in a downstream position with sufficient distance to prevent the incoming fluid from contacting fluid already rotating within the separation chamber. This considerably reduces impact and collisions between fluid streams and impacts of fluid with surfaces within the separation chamber, in turn reducing or minimising fluid shear.

To assist with creating a helical or rotational flow pattern for fluid within the separation chamber, the separation chamber is preferably provided with a fluid guide surface that extends in a helical pattern within the separation chamber. Such a guide surface may be referred to as a 'ramp'. In this way, fluid entering the separation chamber is caused to rotate through contact with the fluid guide surface. The fluid guide surface is preferably used in conjunction with an appropriately angled and oriented inlet, as hereinbefore described.

The choke assembly is adapted for the processing of a multiphase fluid stream. The multiphase fluid stream may comprise two or more liquid phases. Alternatively, the fluid stream may comprise a gas phase and one or more liquid phases. The choke assembly is particularly advantageous when applied to the processing of fluid streams produced from subterranean wells, in particular fluid streams produced from oil and/or gas wells. A typical multiphase fluid stream produced from a well comprises oil, water, most likely in combination with gas. In addition, the multiphase fluid stream may comprise solids, in the form of suspended or entrained solid particles. As noted above, fluid streams produced from subterranean wells typically contain suspended and entrained solid particles, for example sand, grit and larger particles. The choke assembly of the present invention is particularly suitable for the processing and separation of multiphase fluid streams containing solid particles.

The choke assembly may comprise a single inlet for fluid to be processed. Alternatively, the choke assembly may comprise a plurality of inlets for providing fluid to the separation chamber. In particular, the assembly may comprise a first inlet for lighter fluid, such as light liquids, for example oil, and gas, and a second inlet for heavier fluid, such as oil and water. The plurality of fluid inlets are preferably displaced from one another in the longitudinal direction of the separation chamber, with the preferred arrangement being one in which the first inlet for lighter fluid streams is upstream of the second inlet for heavier fluid streams.

The or each fluid inlet may be located adjacent one end, that is the upstream end, of the separation chamber. Alternatively, the or each fluid inlet may be displaced in a downstream direction from the upstream end of the separation chamber. The region of the separation chamber upstream of the inlet can serve to collect light fluids. In this way, when in operation and processing a fluid stream with very light fluid phases, such as gas, the light fluid phases are caused to collect and concentrate in the upstream collection region, for example forming a gas cap.

In a preferred embodiment, the choke assembly comprises a fluid inlet assembly having a curved flow path, most preferably a helical flow path, for fluid entering the separation chamber through the fluid inlet. In this way, the incoming fluid is caused to flow along a helical flowpath before reaching the separation chamber. Separation of the fluid phases will begin to occur prior to the fluid entering the separation chamber, enhancing the separation efficiency of the choke assembly. The curved flow path may be provided by an appropriately curved pipe, for example a helical pipe assembly, or by suitable baffles or other flow directing means within the pipe connected to the inlet. The inlet assembly is preferably oriented with respect to the fluid inlet so that the fluid stream entering the separation chamber is properly oriented to direct the heavier fluid phases into the region of the separation chamber with the higher concentration of heavier fluid and the lighter fluid phases into the region of the separation chamber with the higher concentration of lighter fluid. In particular, when the fluid in the separation chamber is to flow in a circular or helical path, the inlet assembly is oriented to direct the heavier fluid phases to the radially outer regions of the separation chamber and the lighter fluid phases to the radially inner regions of the separation chamber.

The second outlet is disposed to allow removal of fluid that has not left the separation chamber through the choke element. The separation chamber, either by virtue of its form and/or its operation, serves to direct the heavier fluid phases, and any solids present, away from the choke element and towards the second outlet. The separation chamber preferably provides further conditioning of the fluid flow and separation prior to the fluid leaving the chamber through the second outlet.

The second outlet is preferably located in the separation chamber downstream of the choke element. The second outlet operates to remove the heavier fluid phases that have not entered the choke element. When the choke assembly is used to process fluid streams containing solids, solid material will also leave the separation chamber through the second outlet. In order to promote the separation of the lighter and heavier fluid phases and, if present, solid particles, it is preferred that the region of the separation chamber upstream of the second outlet, but downstream of the choke element, is formed to allow gravity-assisted separation to occur. In particular, it is preferred that any solid particles are allowed to settle towards the second outlet.

To assist with allowing gravity separation in the region of the separation chamber upstream of the second outlet, the separation chamber is preferably formed to provide a fluid flowpath of reduced cross-sectional area in the region upstream of the second outlet. This reduced flow area may be provided by having the outer wall of the separation chamber tapered inwards, either continuously or stepwise. Alternatively, or in addition thereto, the separation chamber may be provided with means to reduce the flow area, such as a tapered or conical member disposed co-axially within the chamber. In order to enable further separation of the fluid phases to take place, in particular to allow the lighter fluid phases, especially gas, to separate from the heavier fluid phase flowing towards the second outlet, the means for reducing the flow area is preferably provided with one or more conduits therethrough, to allow lighter fluid phases to flow upstream towards the choke element.

In addition, the separation chamber is preferably provided with means to reduce or prevent fluid rotation within the upstream region adjacent the second outlet. This is particularly preferred when the separation chamber is to operate with a rotational fluid separation regime, as described hereinbefore.

The choke assembly may comprise further means for separating the lighter fluid phases that leave the separation chamber through the choke element. In particular, the choke assembly may comprise further means for separating and removing a gas phase and a light liquid phase. Suitable and preferred means for effecting this separation will be described hereinafter.

In a second aspect, the present invention provides a method of controlling and separating the flow of a multiphase fluid stream, the method comprising:

introducing the multiphase fluid stream into a separation zone;

allowing separation of the fluid phases in the fluid stream to occur in the separation zone;

causing a first portion of the fluid stream to flow through a choke element to a first outlet;

controlling the flow of fluid through the choke element by adjusting the choke element; and causing a second portion of the fluid stream to flow to a second outlet.

In the method of the present invention, the multiphase fluid stream may comprise a combination of gas and liquid phases, and/or a plurality of liquid phases. The method of the present invention is particularly suitable for the processing of multiphase fluid streams containing solid material, for example suspended or entrained solids.

The multiphase fluid stream undergoes separation in the separation zone, resulting in a separation of the fluid phases into relatively lighter fluid phases and relatively heavier fluid phases. Any suitable separation regime may be employed to cause the fluid phases to separate. The fluid stream is preferably caused to rotate in the separation zone, most preferably flowing in a helical pattern, in order to promote the separation of lighter and heavier fluid phases and minimise the amount of shear forces applied to the fluid. The fluid stream is preferably introduced into the separation zone at an angle, in order to promote the rotation of fluid within the zone. Most preferably, the fluid is introduced tangentially into the separation zone. In order to prevent the incoming fluid from impacting the fluid already rotating within the separation zone, the incoming fluid is preferably directed at an angle to the downstream direction, such that fluid rotating within the separation chamber passes the incoming fluid stream without significant impact between the two.

To enhance the rotational fluid separation, the incoming fluid may be preconditioned prior to entering the separation zone by flowing along a circular flow path, most preferably a helical flowpath, to initiate the separation of lighter and heavier phases. If such preconditioning occurs, the preconditioned fluid stream is preferably introduced into the separation zone such that the fluid phases are respectively oriented according to the arrangement of fluid phases within the separation zone. In particular, the incoming fluid stream is preferably oriented with the heavier phases entering closest to the radially outer region of the separation zone and the lighter phases being closest to the radially inner region of the separation zone.

In operation, the lighter fluid phases are caused to pass through the choke element. The lighter fluid phases entering the choke element may contain heavier fluid phases, but in significantly reduced amount compared with the fluid stream at the inlet, that is the fluid entering the choke element will be richer in lighter fluid phases. In contrast, the heavier fluid phases and, if present, solid material, are caused to bypass the choke element and pass towards the second outlet for leaving the separation zone.

The heavier fluid phases remaining in the separation zone and flow towards the second outlet will comprise lighter fluid components, but be rich in the heavier phases. Most preferably, the heavier fluid phases undergo further separation in the separation zone, in order to further remove lighter fluid phases. This separation is most preferably a gravity assisted separation, with any rotation of the fluid stream being damped or hindered by suitable means in the separation zone.

As noted above, the fluid stream is separated in the separation zone into respectively heavier and lighter phases. It is preferred that the lighter phases are caused to flow through the choke element to the first outlet, while the heavier phases remain in the separation zone and flow to the second outlet. Accordingly, in a further aspect, the present invention provides a method of controlling and separating the flow of a multiphase fluid stream, the method comprising:

introducing the multiphase fluid stream into a separation zone;

allowing separation of the fluid phases in the fluid stream to occur in the separation zone;

causing lighter fluid phases separated in the separation zone to flow through a choke element to a first outlet;

controlling the flow of fluid phases through the choke element by adjusting the choke element; and causing the remaining fluid phases to flow to a second outlet.

As described hereinbefore, the methods of the present invention may be operated to provide a single fluid stream as feed to the separation zone. However, in one preferred arrangement, as described above, the choke assembly is provided with a plurality of inlets, in particular a first inlet for lighter fluid phases and a second inlet for heavier fluid phases. Accordingly, the present invention also provides a method of controlling and separating the flow of multiphase fluid streams, the method comprising:

introducing a first fluid stream rich in lighter fluid phases into a separation zone;

introducing a second fluid stream rich in heavier fluid phases into a separation zone to form a combined fluid stream in which the first fluid stream and the second fluid stream are in contact;

allowing separation of the fluid phases in the combined fluid stream to occur in the separation zone;

causing lighter fluid phases separated in the separation zone to flow through a choke element to a first outlet;

controlling the flow of fluid phases through the choke element by adjusting the choke element; and causing the remaining fluid phases to flow to a second outlet.

It is the case that light fluid streams, in particular gas streams, typically have minor portions of heavier fluids, in particular entrained liquid droplets, which are to be removed. Equally, heavier fluid streams, in particular liquid streams such as oil and water, will have minor portions of lighter fluids, in particular entrained gas, which is also to be removed. The method of the present invention allows the lighter and heavier streams to contact in the separation zone, but not intimately mix, and form an interface across which the minor components in each stream can pass. In this way, the heavier fluid components, in particular liquid, leave the first, lighter fluid stream. Similarly, the lighter fluid components present in the second, heavier fluid stream pass across the interface to collect in the lighter fluid stream.

As noted previously, it is preferred that the first fluid stream is introduced into the separation zone upstream of the second fluid stream. This allows a stable fluid-fluid interface to be formed rapidly and maintained. Both the first and second fluid streams are preferably caused to rotate within the separation zone, as hereinbefore described, to enhance separation. Either one or both fluid streams may be preconditioned to initiate separation prior to entry into the separation zone, again as hereinbefore described.

The choke element receives fluid that has been separated into lighter and heavier phases. In a preferred arrangement, the lightest fluid phases, in particular gas, enters the choke element in the most upstream portion, with the heavier fluid phases, in particular light liquid phase, entering in the adjacent downstream portion and, if present, heaviest fluid phases entering the most downstream portion of the choke element. This flow scheme offers significant advantages in the operation of choke assemblies having further separation means downstream of the choke element, as described below.

As described hereinbefore, it is advantageous to provide the choke assembly with a plurality of fluid inlets, in particular a first inlet for a lighter fluid stream and a second inlet for a heavier fluid stream. Accordingly, the present invention also provides a choke assembly comprising:

a choke element for controlling the flow of fluid therethrough;

a first inlet for a lighter fluid stream;

a second inlet for a heavier fluid stream; and at least one outlet for fluid.

In addition, the present invention also provides a method for controlling the flow of fluid, the method comprising:

introducing a first, light fluid stream into a choke assembly through a first inlet;

introducing a second, heavy fluid stream into the choke assembly through a second inlet;

allowing the first and second fluid streams to come into contact;

passing fluid from the first and second streams through a choke element to control the flow of fluid; and removing fluid from the choke assembly through at least one outlet.

As noted above, the choke assembly of the present invention may comprise means for separation of the fluid stream that has passed through the choke element. Accordingly, in a further aspect, the present invention provides a choke assembly comprising:

an inlet for a multiphase fluid stream;

a choke element;

a separation chamber located downstream of the choke element to receive fluid passing through the choke element;

a first outlet in the separation chamber for a first fluid stream; and a second outlet in the separation chamber for a second fluid stream.

This separation means for the fluid stream is preferably in addition to the features of the choke assembly described hereinbefore, in particular the separation features upstream of the choke element.

The choke element may have any suitable design and configuration to provide the necessary control of the fluid stream passing therethrough to the outlets. A most suitable arrangement for the choke element is a plug and cage assembly, as discussed hereinbefore, preferred embodiments of which are described hereinafter.

In the choke assembly of this aspect of the present invention, the separation chamber may have any suitable configuration. It is preferred that the separation chamber is arranged to allow separation to occur as a result of the rotational flow of the fluids therein, in particular by having the fluid stream flow in a helical pattern. Any suitable means may be provided to promote the rotational or helical fluid flow pattern. Preferably, the components of the choke element are adapted to induce a rotational flow pattern in the separation chamber. Suitable and preferred choke elements are described hereinafter.

In the choke assembly, a first outlet for fluid is provided. This outlet is for lighter fluid phases, in particular gaseous phases. A second outlet is provided in the separation chamber for the remaining fluid, in particular heavier fluid phases.

In one preferred embodiment, the separation chamber extends within the choke element. This arrangement is particularly preferred when operating the assembly to control and separate fluid streams comprising a significant gas phase. The separation chamber is preferably arranged so that, in operation, gas collects in the upstream region of the separation chamber and forms a gas cap. Gas collected in the gas cap leaves the separation chamber through the first outlet, while liquid remaining in the separation chamber exits through the second outlet.

In a preferred arrangement, the choke element comprises a stem connected to a choke actuator or drive mechanism. This arrangement is particularly preferred when using a choke element of the plug and cage type, in which the plug is moved longitudinally within the cage by means of a stem connecting the plug to an actuator or suitable drive means. The stem of the choke element is formed with a central bore, and provides the first outlet for fluid from the separation chamber, in particular for gas.

As heavier fluids can be entrained in the lighter fluid phase leaving through the first outlet, the choke assembly may be provided with a further separation means for removing such entrained heavier fluids. The separation means preferably comprise an inlet for lighter fluid, connected to the first outlet from the separation chamber, and a second separation chamber having a first outlet for lighter fluid phases, in particular gas, and a second outlet for heavier fluid phases. Most preferably, the separation means are arranged to provide, in operation, a rotational flow of fluids within the second separation chamber, whereby the heavier liquid phases are collected in and removed from the radially outer regions of the second separation chamber and the lighter fluid phases are collected in a removed from the radially inner regions of the second separation chamber.

Fluids, in particular heavier fluid phases, remaining in the separation chamber flow to the second outlet, through which they exit. Preferably, the choke assembly comprises a means to inhibit or prevent the formation of a stable vortex in the fluids in the region of the separation chamber adjacent and upstream of the second outlet. Suitable means for arresting or preventing vortices are known in the art and include a vortex breaker. The need for a vortex breaker is particularly great when the fluids being separated in the separation chamber include gas, which is removed through the first outlet, and the separation occurs using rotational flow of the fluids.

The separation chamber may have any suitable configuration and shape. In a preferred arrangement, the chamber is formed to have an increasing cross-sectional area to fluid flow in the region upstream and adjacent the second outlet.

As noted, one preferred embodiment of the present invention provides a means for removing a light fluid phase, in particular a gas, from the choke assembly through the stem of the choke element. Accordingly, in a further aspect, the present invention provides a choke assembly comprising:

a choke element comprising a moveable choke component;

a stem connected to the moveable choke component;

wherein the stem has a bore therethrough to provide an outlet for fluid from within the choke element.

The separation means downstream of the choke element for fluid passing through the choke may comprise further separation means for separating two liquid phases, either as an alternative to or in addition to the separation described previously in which a lighter fluid phase, in particular a gas is removed. The further separation means are preferably disposed in the separation chamber downstream of the choke element and provide an outlet for a first liquid phase and an outlet for a second liquid phase. One preferred arrangement is employed in conjunction with a rotational separation regime, in which the fluids in the separation chamber are caused to rotate. As described, under the action of the rotating fluids, the lighter fluids are caused to collect in the radially central region of the separation chamber. In such a case, an outlet is preferably disposed in the radially central region of the separation chamber, in order to remove the lighter liquid phase. The outlet is most preferably disposed at the longitudinal axis of the separation chamber in the form of a longitudinal conduit extending co-axially within the separation chamber. The conduit is preferably provided with a plurality of openings, through which the lighter liquid phase may pass to enter the conduit. It is preferred that the openings extend at an angle to the radial direction of the conduit, most preferably tangentially, in order to provide a flowpath that subjects the liquids to minimum shear.

Heavier liquid phases collected at the raidally outermost regions of the separation chamber are removed through an outlet disposed in the outermost wall of the separation chamber. Again, this outlet is most preferably arranged at an angle to the radial direction of the separation chamber, especially tangentially.

The present invention provides in a further aspect, a method for controlling and separating a multiphase fluid stream, the method comprising:

passing the fluid stream through a choke element and controlling the flow of fluid using the choke element;

introducing the fluid stream into a separation zone and causing phases of the fluid stream to separate;

removing a lighter fluid phase from the separation zone through a first outlet; and removing a heavier fluid phase from the separation zone through a second outlet.

Separation in the separation zone may take place using any suitable regime. However, it is preferred that the separation takes place using a rotational fluid flow, in particular a helical fluid flow through the separation zone. In this way, heavier fluid phases are caused to collect in the radially outermost regions of the separation zone, while lighter fluid phases collect in the inner radial regions. In a preferred embodiment, the separation zone extends within the choke element. In particular, the lighter fluid phases, especially gas, is allowed to collect within the upstream region of the choke element, from where it is removed through the first outlet. A most convenient method removes the lighter fluid phases from the separation zone within the choke element through the stem of the choke assembly. Accordingly, the present invention also provides a method for controlling and separating a multiphase fluid stream, the method comprising:

passing the fluid stream through a choke element and controlling the flow of fluid using the choke element;

introducing the fluid stream into a separation zone and causing phases of the fluid stream to separate; and removing a lighter fluid phase from the separation zone through an actuation stem extending from the choke element.

The method may further comprise separating heavier fluid phases, in particular liquid phases within the separation zone downstream of the choke element. Any suitable separation regime may be used to separate the liquid phases. Most preferably, a rotational flow regime is employed, in particular with the fluids flowing in a helical pattern, whereby the lighter liquid phases collect in the radially innermost region of the separation zone and the heavier liquid phases collect in the radially outermost regions. The lighter liquid phases are removed from the innermost region, most preferably through a conduit extending longitudinally within the separation zone. The heavier liquid phases are preferably removed from the outer region of the separation zone, especially through an outlet arranged at an angle, preferably tangentially, to the separation zone.

As noted above, the present invention provides significant improvements in the design and arrangement of choke elements, in particular choke elements of the plug and cage type. In this variety of choke assembly, the cage is provided with a plurality of openings therethrough to allow the passage of fluid. The plug is moveable with respect to the cage and, by overlying the openings, is used to open or close the openings according to the flow control requirements of the choke. The plug is moved with respect to the cage between an open position, in which all of the openings in the cage are uncovered and are open for the passage of fluid therethrough, and a closed position in which all openings in the cage are covered and closed to fluid flow. Movement of the plug with respect to the cage between the open and closed positions successively opens or closes the openings, depending upon the direction of movement.

A particularly preferred choke assembly is one in which the openings in the cage extend at an angle to the radial direction of the cage, most especially at a tangent to the cage. In this way, the fluid passing through the cage is caused to enter a rotational flow regime within the cage and downstream thereof. The angled or tangential entry of fluid into the choke cage reduces the impact of the individual fluid streams entering through a plurality of openings and, hence, significantly reduces the degree of shear to which the fluids are subjected. In this way, any separation of fluid phases that has occurred or been initiated upstream of the choke element is not affected. In addition, by causing the fluids to follow a curved or tangential path within the choke cage, the direct impact of entrained and suspended solid particles entering the cage on the opposing inner wall portion of the cage are reduced or eliminated. In this way, damage to or destruction of the choke cage is significantly reduced.

The rotational fluid flow pattern generated by the angled or tangential flow of fluids within the cage is of particular use with the downstream separation of the fluids, as described hereinbefore.

In a first aspect relating to choke elements, the present invention provides a choke assembly comprising a choke element comprising:

a cage having a plurality of openings therethrough for the passage of fluid;

a plug moveable with respect to the cage to open and close the openings in the cage;

wherein the openings in the cage extend tangentially to the cage, each opening comprising an outer portion extending from the outer surface of the cage having a first cross-sectional area and an inner portion extending from the inner surface of the cage having a second cross-sectional area, the first cross-sectional area being greater than the second cross-sectional area.

The openings are shaped to decrease in cross-sectional area in the inwards direction. In this way, the fluid passing through the cage is caused to pass along an increasingly smaller conduit, thereby increasing its velocity. This serves to assist with the formation of a rotational fluid flow pattern within the choke element and downstream thereof, while at the same time reducing the degree of shear to which the fluid is subjected. The openings may have a step-wise change in cross-sectional area. More preferably, in order to reduce the shear to which the fluid is subjected, the changes in cross-sectional area are gradual or continuous.

The form of the openings, having an outer portion that is wider and providing a greater cross-sectional area for fluid flow than the inner portion, is advantageous when used with a choke element that has two, concentric portions. This form of choke element has an inner, generally cylindrical choke portion of a hard, resistant material, such as tungsten. A generally cylindrical outer portion extends coaxially around the inner portion and may be formed of a less resistant material, such as stainless steel. The form of opening allows the fluid to pass through the outer, less resistant portion at a lower velocity and only have a higher, more erosive velocity when passing through the inner choke portion.

As noted, the openings through the cage are shaped, such as being tapered or curved, with the cross-sectional area of the opening reducing in the inwards direction. A tapered opening having substantially straight or linear sides is easier to form in the cage than a curved opening. While more difficult to fabricate, openings with a curved profile may be preferred as they provide an optimum flow pattern of fluid through the cage elements. The openings may each be symmetrical about their central axis extending through the cage. However, in one preferred arrangement, the openings are offset, such that the outer end of the opening, having the widest cross-sectional area, extends in a direction upstream of the flow of fluid past the choke cage when in operation. This has the effect of reducing the shear experienced by the fluid as it enters the opening in the cage.

In one preferred arrangement, the choke cage is formed from an inner choke cage element and an outer choke cage element, arranged concentrically around the inner choke cage element. The inner and outer choke cage elements are formed with corresponding openings to provide passage for fluid through the cage. The outer choke cage element may be formed with openings having the first, greater cross-sectional area and the inner choke cage element may be formed with openings having the second, lesser cross-sectional area. In one embodiment, the openings in the outer cage element taper inwardly. The openings in the inner choke cage element may have a constant cross-sectional area along their length through the element.

The ratio of the first and second cross-sectional areas is preferably in the range of from 1:1.5 to 1:5, more preferably from 1:2 to 1:3. The openings are sized to provide a graduated, most preferably a smooth, gradual, entry for the fluid rotating around the outside of the cage to the tangentially arranged opening and into the inner region of the cage.

In a further aspect of the present invention relating to choke elements, there is provided a choke assembly comprising a choke element comprising:

a cage having a plurality of openings therethrough for the passage of fluid;

a plug moveable with respect to the cage to open and close the openings in the cage;

wherein the openings in the cage extend tangentially to the cage, the cage comprising openings arranged in a plurality of bands extending circumferentially around the cage, the cross-sectional area of the openings of the bands increasing in the upstream direction of the cage.

The arrangement of the openings into bands allows for an accurate control of the flow of fluid through the choke, by positioning the plug with respect to the cage accordingly. In operation, the most downstream band of openings is the last to be covered when the choke is being closed and the first to be uncovered when the choke is being opened. In this way, as the choke is opened and each successive band of openings is uncovered, the cross-sectional area available for the flow of fluid increases by an increasing amount with successive bands.

Each band may have a different cross-sectional area of openings than those adjacent to it. Alternatively, the bands may be grouped, such that all the bands in a given group have the same cross-sectional opening area, but have a greater area than the bands in the adjacent downstream group. In a preferred embodiment, the bands are in groups of two, such that each pair of bands differs in cross-sectional area of openings to each adjacent pair of bands.

The openings in a given band preferably have the same cross-sectional area. In one embodiment, all the openings in the bands have the same cross-sectional area and the difference in the cross-sectional area of openings between bands is achieved by varying the number of openings in successive bands or groups of bands. For example, in one preferred arrangement, each band in the most downstream pair of bands have two openings. The bands in the adjacent pair of bands each have four openings. The adjacent upstream pair of bands each have 8 openings.

It is preferred that the openings in adjacent bands are offset circumferentially with respect to one another, in particular where adjacent bands are in the same group and have the same number of openings.

In the choke assemblies of the present invention, the plug and cage are moveable with respect to one another. Preferably, the cage is fixed and the plug is moveable with respect to the cage. In a very typical arrangement, the plug is arranged concentrically with respect to the cage and moves longitudinally along the central axis shared by the plug and cage. The plug may be disposed outside or inside the cage, with the plug being disposed inside the cage preferred.

It has been found that the arrangement of openings in the cage into bands allows for a different choking regime to be achieved within the choke cage than known choke assemblies. In the known arrangements of choke assemblies, the flow of fluid through the choke elements is controlled or choked by varying the cross-sectional area of the openings in the choke element, in particular the cage, through which the fluid must flow. This choking regime relies upon the physical barrier presented by the choke cage to the flow of fluid. It has now been found that an alternative regime may also be employed. In particular, the passage of fluid through bands of angled openings, especially tangential openings, in the choke cage establish for each band of openings a band or ring of rotating fluid within cage. The shape adopted by the rotating fluid in the cage is generally toroidal. Fluid entering through an opening in an upstream band must flow past the rotating fluid band or ring established by a downstream band of openings. It has been found that the fluid is caused to move radially inwards to pass the downstream band, that is the rotating band of fluid causes an effective reduction in the cross-sectional area of the interior of the cage available for fluid flow. The use of a plurality of bands of openings to generate a corresponding plurality of rotating bands of fluid can provide an effective regime for choking and controlling the flow of fluid through the choke assembly. This use of the fluid itself to limit or control the cross-sectional area available for fluid flow provides an effective choking mechanism, while subjecting the fluid to very low rates of shear.

The change in direction of flow of the fluid in this way is accompanied by a change in momentum of the fluid stream, which in turn creates a resistance to the flow of fluid or a back pressure, allowing the flowrate of the fluid stream through the choke assembly to be controlled.

Accordingly, in a further aspect, the present invention provides a method of controlling the flow of a fluid, the method comprising:

introducing the fluid into a flow control zone having a general downstream direction in which the fluid is required to flow, the fluid being introduced into the flow control zone through a plurality of openings; wherein fluid introduced through a first group of openings, downstream of a second group of openings, establishes a generally toroidal flow pattern within the flow control zone, whereby the effective cross-sectional area available for the flow of fluid introduced through the second group of openings in the downstream direction is reduced.

The first group of openings may comprise a single opening, or more preferably a plurality of openings, in order to establish the toroidal flow pattern within the flow control zone. The openings are such that the fluid enters at an angle to the radial direction of the flow control zone, most preferably tangentially into the flow control zone.

The openings in the second group may be such that fluid introduced into the flow control zone through these openings is caused to form a second toroidal flow pattern, providing a further reduction in the effective cross-sectional area available for the flow of fluid introduced upstream of the second group. Third and further groups of openings may be employed to generate further toroidal flow patterns.

As noted previously, the methods and apparatus of the various aspects of the present invention are particularly suitable for use in the processing of fluid streams produced from subterranean wells, in particular fluid streams produced from oil and gas wells. Accordingly, in a further aspect, the present invention provides an installation for the processing of fluid streams produced from a subterranean well comprising an assembly as hereinbefore described. The efficient separation of fluid streams produced from subterranean wells, in particular the separation of gas, water and oil phases from a produced fluid stream, is particularly important in the case of subsea wells. It is commonly the case that water produced from a well is required to be separated from co-produced oil and gas and pumped back into the subterranean formations. The choke assemblies of the present invention may be advantageously applied in the separation of water from a fluid stream produced from a subsea well, allowing the water to be returned to the underground formations without the need for the fluid stream to be produced all the way to the surface of the sea. Accordingly, the present invention also provides a subsea installation comprising a choke assembly as hereinbefore described.

BRIEF DESCRIPTION OF THE DRAWINGS

Embodiments of the present invention will now be described, by way of example only, having reference to the accompanying drawings, in which:

FIGS. 13a to 13f are cross-sectional views through the choke cage of the choke element of FIG. 11 along the lines Section A, Section B, Section C, Section D, Section E and Section F, respectively.

DETAILED DESCRIPTION OF THE DISCLOSED EMBODIMENTS

Figure 1:
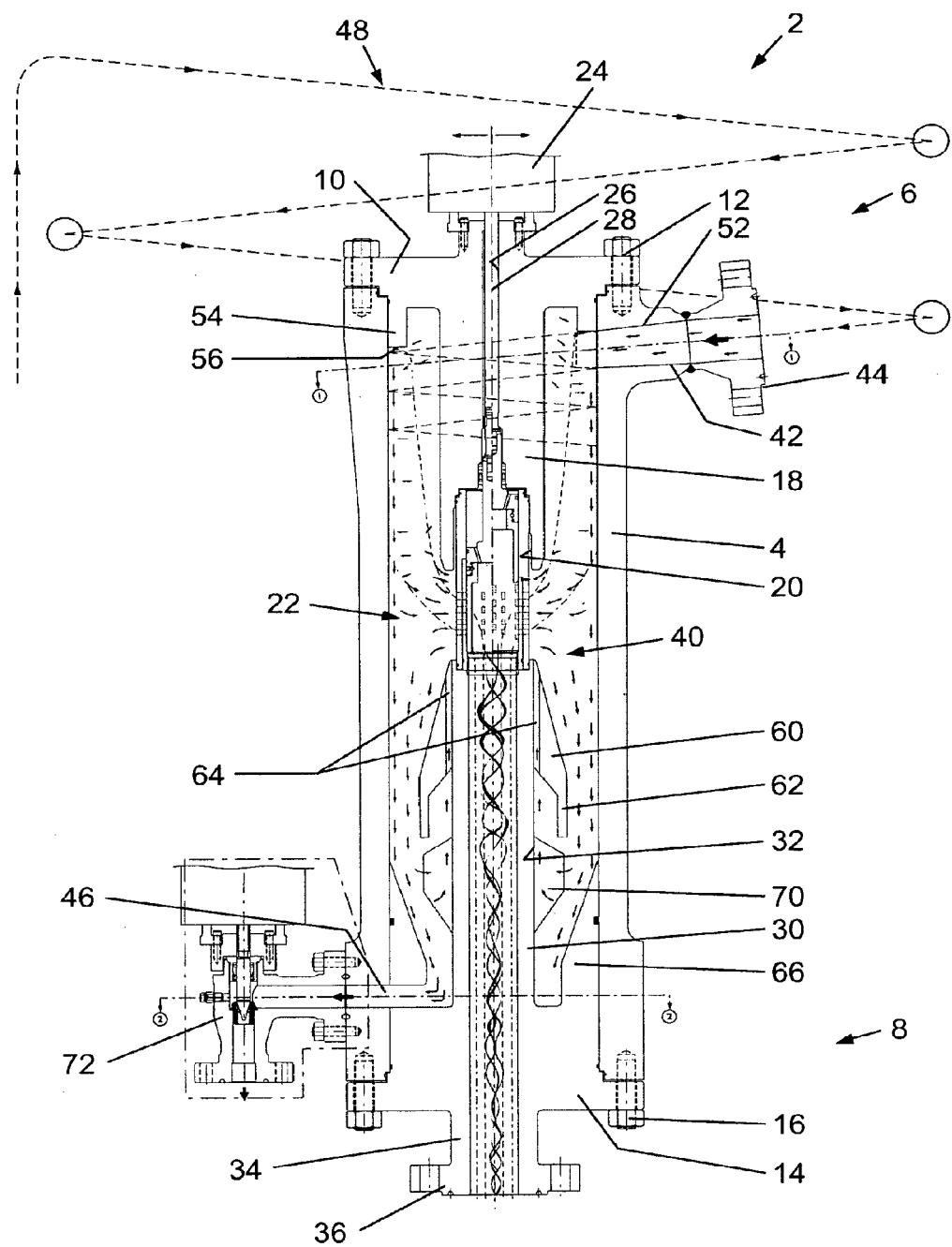
FIG. 1 is a cross-sectional view of a first embodiment of a choke assembly of the present invention.
Figure 2:
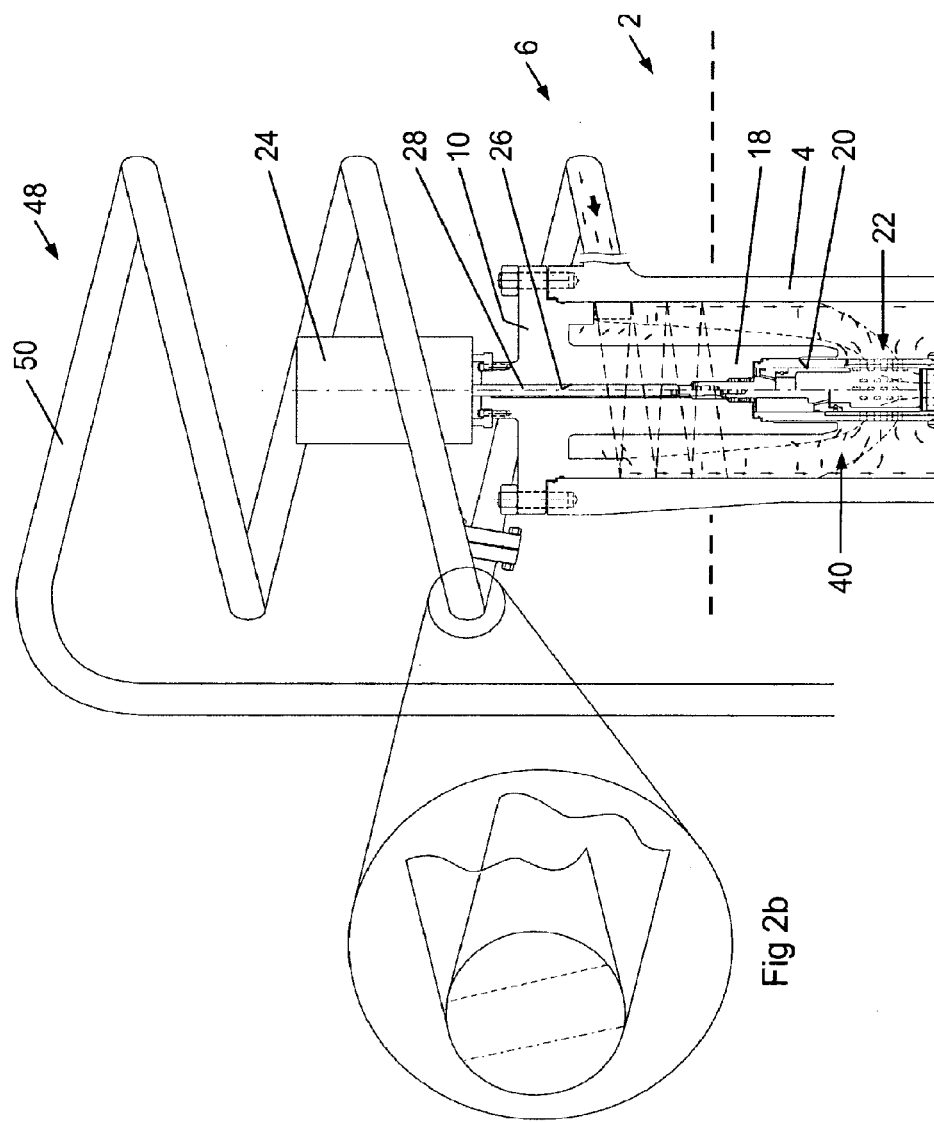
FIG. 2a is a cross-sectional view of the upper portion of the choke assembly of FIG. 1, with the inlet assembly shown in greater detail.
FIG. 2b is a representation of the fluid flow pattern in a portion of the inlet assembly.
Figure 11:
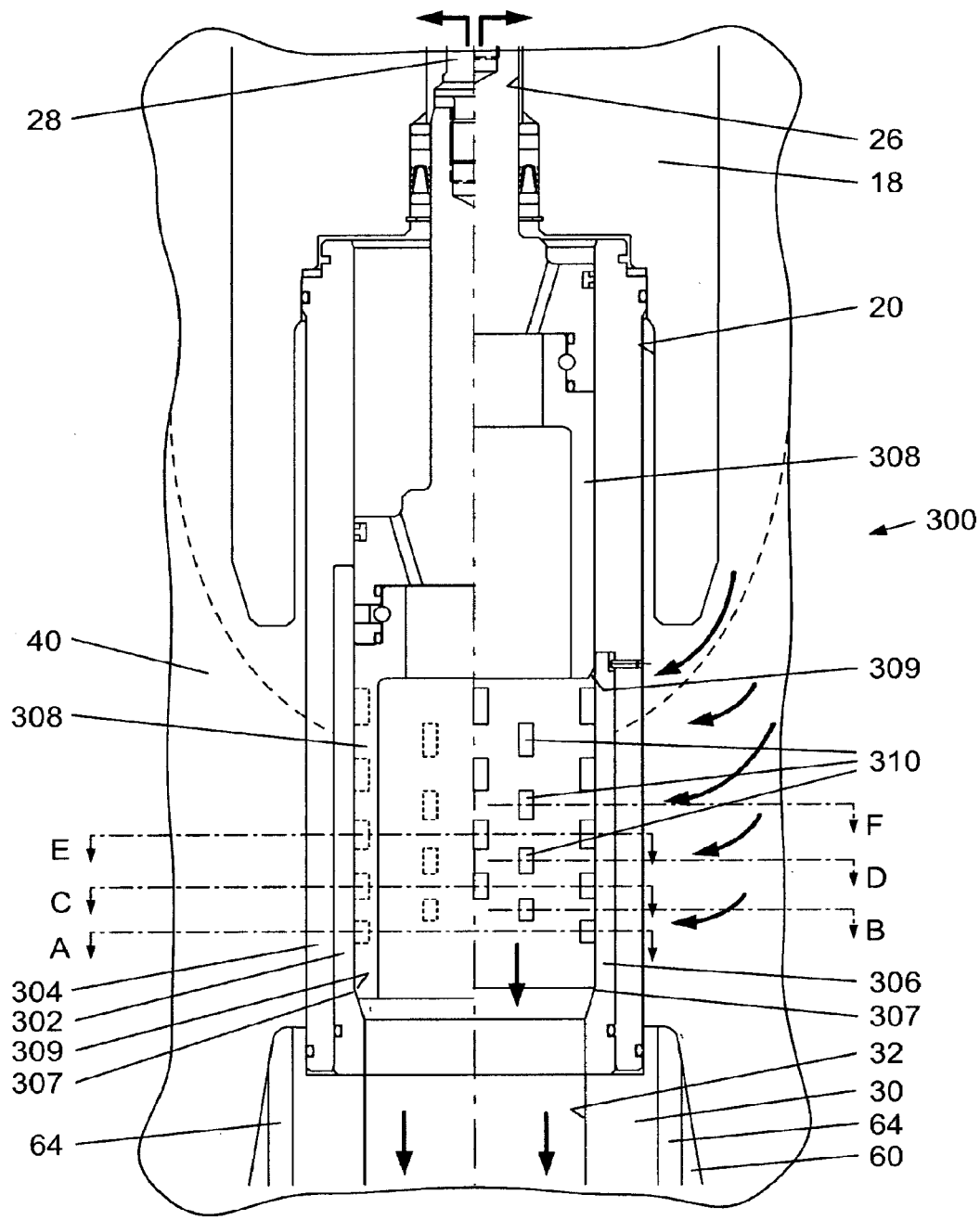
FIG. 11 is a cross-sectional view of a choke element of the present invention.

Referring to FIGS. 1 and 2a, there is shown a choke assembly, generally indicated as 2. The choke assembly comprises a generally cylindrical housing 4 having an inlet end, generally indicated as 6, and an outlet end, generally indicated as 8. A first cap 10 is mounted on the housing 4 by bolts 12 to enclose the inlet end 6. A second cap 14 is mounted on the housing 4 by bolts 16 to enclose the outlet end of the housing. The first and second caps 14, 16 are formed to provide several additional functions, as follows:

The first cap 10 has a central mandrel 18 extending therefrom coaxially within the housing 4, the distal end of the mandrel 18 being formed with a cylindrical recess 20 to provide a housing and support for the upper portion (as viewed in FIG. 1) of a choke element, generally indicated as 22. The choke element may be of any conventional design, with the arrangement shown in FIG. 1 being of a plug and cage type. The details of a preferred choke element are shown in FIG. 11 and described hereinafter. An actuator 24 is mounted to the exterior of the first cap 10 in conventional manner. The first cap 10 and mandrel 18 are provided with a central longitudinal bore 26, extending from the actuator 24 to the cylindrical recess 20, through which extends an actuator stem 28. The actuator stem 28 is connected to the plug of the choke element 22, again in conventional manner, and provides means for the actuator 24 to move the plug longitudinally within the choke cage. The second cap 14 has a central mandrel 30 extending therefrom coaxially within the housing 4, the distal end of the mandrel 30 being formed to support the lower portion (as viewed in FIG. 1) of the choke element 22. The central mandrel 30 and second cap 14 have a large bore 32 extending longitudinally therethrough. At its inner end, the bore 32 opens into the central cavity within the choke element. At its outer end, the bore 32 extends through an outlet nozzle 34 formed on the exterior of the second cap 14, terminating in a flange 36 of conventional design. In this way, the bore 32 provides a conduit for fluid passing through the choke element 22 to leave the choke assembly 2.

As will be seen in FIG. 1, the mandrels 18, 30 and the choke element 22, together with the inner surface of the housing 4, define a generally annular cavity which, in operation, serves as a separation chamber 40. An inlet nozzle 42 for fluid to be processed is provided in the inlet end 6 of the housing 4, terminating in a flange 44 of conventional design. The housing is provided with an outlet 46 for fluid extending through the housing wall adjacent the second cap 14 at the outlet end 8. The details of the separation chamber 40, the inlet nozzle 42 and the outlet 46 will now be described in more detail.

A fluid inlet assembly 48 is connected to the inlet nozzle 42 by way of the flange 44, the generally arrangement of which is shown in dotted lines in FIG. 1 and in detail in FIG. 2a. The inlet assembly 48 comprises a helically extending pipe 50, with the pipe being angled to allow solid material to move along the pipe towards the inlet aided by gravity. The angle of the pipe 50 will be determined by that required to ensure movement of the solids content of the fluid stream being processed. Typically, the pipe 50 will be at an angle of from 5 to 25°, more preferably about 10°. In operation, the inlet assembly 48 provides a pre-conditioning for the multiphase fluid stream being processed. The flow of fluid through the helical path within the pipe 50 causes separation of the heavier and lighter phases in the stream to begin, with the heavier phases collecting at the radially outer region of the pipe bore and the lighter phases moving towards the radially inner region of the pipe bore. FIG. 2b shows a representation detail of the fluid phase separation that is initiated in the bore of the pipe 50 of the inlet assembly 48.

Figure 3:
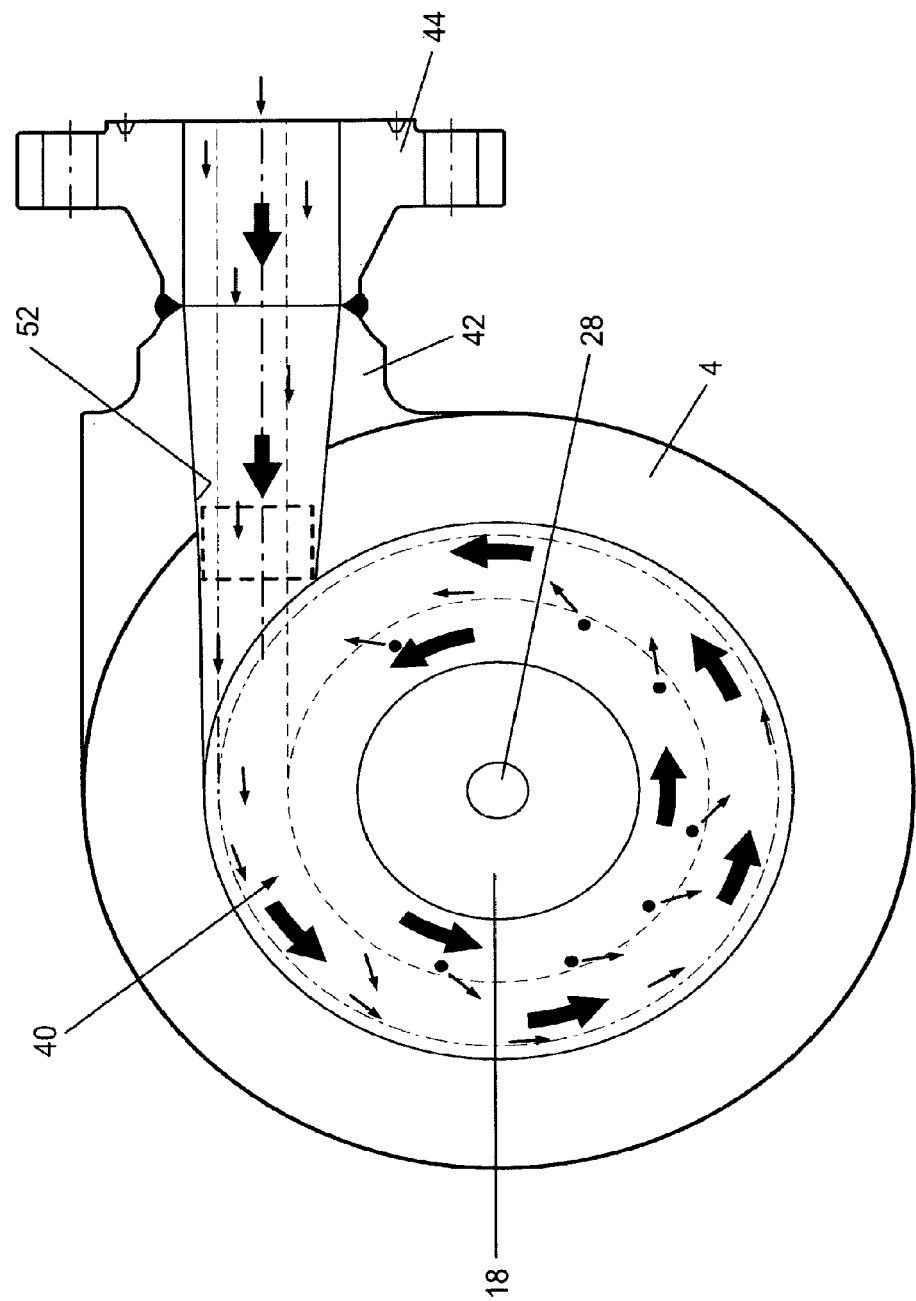
FIG. 3 is a cross-sectional representation of the fluid flow pattern within the choke assembly of FIG. 1 along the line I-I.

The inlet assembly 48 is arranged such that fluid entering the separation chamber 40 through the inlet nozzle 42 is correctly oriented with respect to the fluid within the separation chamber. The orientation of the fluid entering the separation chamber 40 is shown in FIG. 3, which is a cross-sectional representation of the inlet end 6 of the separation chamber 40 and the inlet nozzle 42. The incoming fluid is oriented to have the heavier phases introduced adjacent the inner wall of the housing 4 and the lighter phases introduced towards the central longitudinal axis of the housing 4.

Figure 4:
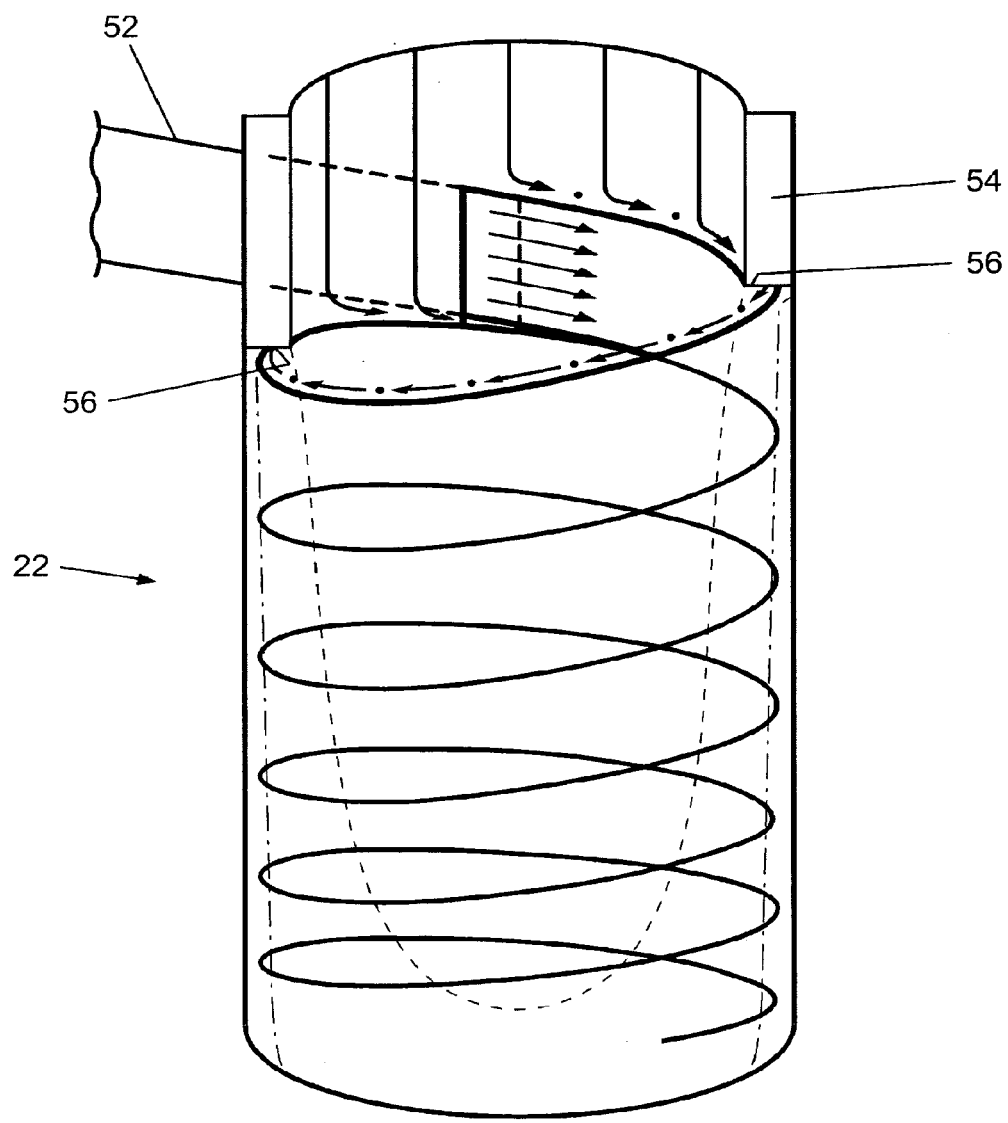
FIG. 4 is a representation of the fluid flow pattern within the separation chamber of the choke assembly of FIG. 1.

The components at the inlet end 6 of the choke assembly 2 are arranged to create a descending helical flow pattern for the fluid within the separation chamber 40. As shown in FIG. 3, the inlet nozzle 42 is arranged to open tangentially into the separation chamber 40. The inlet nozzle 42 has a rectangular bore 52 inclined at an angle to the longitudinal axis of the housing 4 of about 85°, that is an angle of 5° from normal to the longitudinal axis of the housing. Other angles of entry may be used, depending upon the nature of the fluid stream to be processed and the overall geometry of the separation chamber 40. The angle of entry may, for example, range from 0 to 25°. This angled entry ensures that fluid entering the separation chamber is caused to follow a helical path downstream within the separation chamber 40. The helical flow pattern of the fluid entering the separation chamber is represented in FIG. 4. The angle of entry is selected to ensure that the incoming fluid is not brought into direct contact with the rotating fluid already in the separation chamber, but rather that the entering fluid, upon completing one revolution within the separation chamber 40 is caused to pass downstream of the inlet bore 52. To further assist with establishing the helical fluid flow pattern and to reduce contact between the incoming fluid and fluid rotating within the separation chamber, the end cap 10 is formed with a projection 54 extend along the wall of the housing adjacent the inlet nozzle 42. The projection 54 presents a helical surface 56 to the incoming fluid, forcing the fluid to flow in a helical path within the separation chamber 40. The general form of the helical surface 56 is known in the art and described in GB 2353236A.

It will be noted from FIG. 1 that the inlet bore 52 opens into the separation chamber at a distance from the end cap 10. This provides a volume of the separation chamber between the inlet bore 52 and the end cap 10. This volume is of use when processing a fluid stream containing gas and permits the formation of a gas cap in the separation chamber 40 during operation, as will be described hereinafter.

The separation chamber 40 comprises two outlets for fluid. First, fluid may leave the separation chamber through the choke element 22, as will be described hereinafter. Fluid that does not exit through the choke element 22 is removed from the separation chamber 40 through the outlet 46. In the region of the separation chamber 40 downstream of the choke element 22, that is between the choke element and the outlet 46, the choke assembly 2 is provided with features to encourage further fluid phase separation. The choke assembly 2 is configured to reduce the cross-sectional area of flow available within the separation chamber as fluid approaches the outlet 46.

This may be achieved in a number of ways. Referring to FIG. 1, a frusto-conical flow guide 60 is disposed around the central mandrel 30 in the region downstream of the choke element. The effect of the flow guide 60 is to reduce the cross-sectional area available for the flow of fluids in the annular cavity between the mandrel 30 and the inner wall of the housing 4. A generally cylindrical skirt 62 extends in the downstream direction from the downstream end of the flow guide 60. A plurality of longitudinal conduits 64 extend through the flow guide adjacent the mandrel 30 and serve to connect the region of the separation chamber 40 downstream of the flow guide with the upstream region.

As an alternative or in addition to the frusto-conical flow guide 60, the housing 4 may be provided with a conical or tapered form in the region of the separation chamber 40 immediately downstream of the choke element 22.

Figure 5:
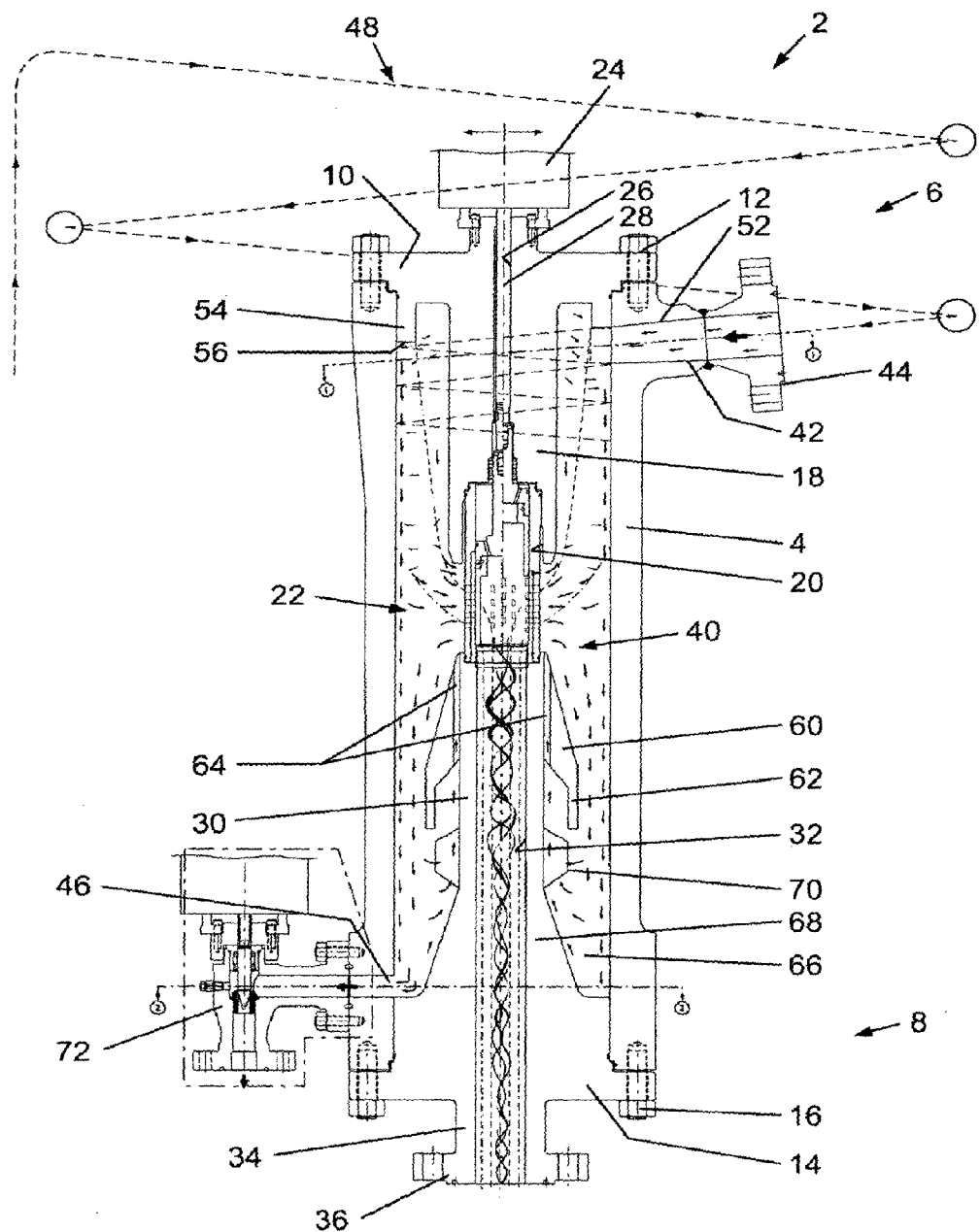
FIG. 5 is a cross-sectional view of a second embodiment of a choke assembly of the present invention.

Downstream of the flow guide 60 and adjacent the outlet 46, the cross-sectional area of the separation chamber 40 is further reduced by a tapered flow guide 66, extending upwards (as viewed in FIG. 1) within the housing 4 from the second cap 14. An alternative to the tapered flow guide 66 of FIG. 1 is shown in FIG. 5. The features of the choke assembly of FIG. 5 common to those of FIG. 1 are indicated using the same reference numerals. The choke assembly of FIG. 5 has the mandrel 30 formed with a tapered section 68 in the region adjacent the end cap 14 and the outlet 46, such that the cross-sectional area of the separation chamber 40 reduces in the downstream direction along the tapered section 68.

Downstream of the flow guide 60, the choke assembly 2 is provided with a plurality of vanes 70 extending longitudinally along the mandrel 30. The vanes 70 act to inhibit the rotation of the fluid in the central zone within the adjacent region of the separation chamber. In this region, it is preferred to maintain some rotational components to the fluid flow, in order to maintain the fluid in an agitated state, for example to ensure entrained solids are kept in suspension.

The flow of the fluid stream leaving the separation chamber 40 through the outlet 46 is controlled by a flow control assembly 72, of conventional design.

In operation, the choke assembly of FIGS. 1 and 5 functions as follows:

The operation of the choke assembly will be described having reference to a multiphase fluid stream comprising gas, oil, water and entrained solid particles, typical of a fluid stream produced from a subterranean well. In this fluid stream, the lightest fluid phase is the gas. Of the liquid phases, oil is the lighter phase and water is the heavier phase. The solid material, as it is entrained in the fluid, will behave as the heaviest fluid stream. It will be understood that this fluid stream is merely exemplary of the fluid streams that can be processed using the choke assembly of this invention and the scope of the present invention is not to be limited to such fluid streams.

The fluid stream is introduced into the inlet end 6 of the separation chamber 40 through the inlet bore 52 of the inlet nozzle 42 from the inlet assembly 48. The action of the inlet assembly 48 has been to precondition the fluid stream and initiate separation of the fluid phases. The fluid is introduced into the separation chamber 40 as shown in FIG. 3, such that the water and entrained solids are concentrated at the inner wall of the housing 4, with oil and gas being introduced into the separation chamber 40 at some distance from the wall. This orientation of the fluid phases matches that assumed by the various phases within the separation chamber 40. The effect of the angle of entry of the fluid and the helical fluid guide surface 56 is to cause the fluid to flow in a helical pattern, moving generally downstream in the separation chamber 40, as represented in FIG. 4. The gas separates from the liquid phases and forms a central gas core, stabilised by a gas cap formed in the inlet end 6 of the separation chamber 40 above (as viewed in FIG. 1) the inlet 52 and adjacent the end cap 10. A gas/liquid interface will form within the separation chamber 40, as represented in FIG. 4, with the liquid phases forming a lining around the wall of the separation chamber 40, surrounding a gaseous core. The interface will have the general 'bowl' shape shown in FIG. 4. Within the liquid phases, oil will collect in the region adjacent the gas/liquid interface, while water and entrained solids will concentrate and migrate to the radially outer region of the separation chamber 40 adjacent the inner wall of the housing 4. The action of maintaining a gaseous core within the liquid 'bowl', prevents liquids and entrained solids from collecting in the central region of the separation chamber. This in turn requires the liquids and entrained solids to collect in the radially outer region, adjacent the wall of the separation chamber, where they are subjected to higher centrifugal forces, further enhancing separation of the phases.

The choke element 22 is located within the separation chamber 40 such that the gas/liquid interface intersects the choke cage, allowing the lighter fluid phases, in particular gas and oil, to leave the separation chamber through the choke element. Some water and solid particles may be entrained with the gas, oil and water stream and leave through the choke element. However, a portion of the water with a concentration of solid material remains in the separation chamber 40. The fluid stream passing through the choke element 22 enters the bore 32 in the mandrel 30 and leaves the choke assembly 2 through the outlet 34 in the end cap 14.

The heavier fluid phases, in particular water and entrained solids pass downstream of the choke element 22 and pass the conical flow guide 60. The decreasing cross-sectional area within the separation chamber 40 as the fluid flows downstream causes the density of solids to increase in the fluid phase. The skirt 62 extending from the flow guide 60 provides a calm region immediately downstream of the flow guide 60. Lighter fluids, in particular gas and oil, entrained with the water and solids collect beneath (as viewed in FIG. 1) the flow guide 60 and flow upwards through the conduits 64 to pass through the choke element 22. Rotation of the water/solid mixture downstream of the flow guide 60 is damped by the vanes 70, allowing the separation of lighter and heavier fluid phases and solid material to occur through a combined rotation and gravity separation regime. Water and solid material are withdrawn from the separation chamber 40 through the outlet 46, under the control of the flow control assembly 72.

Figure 6:
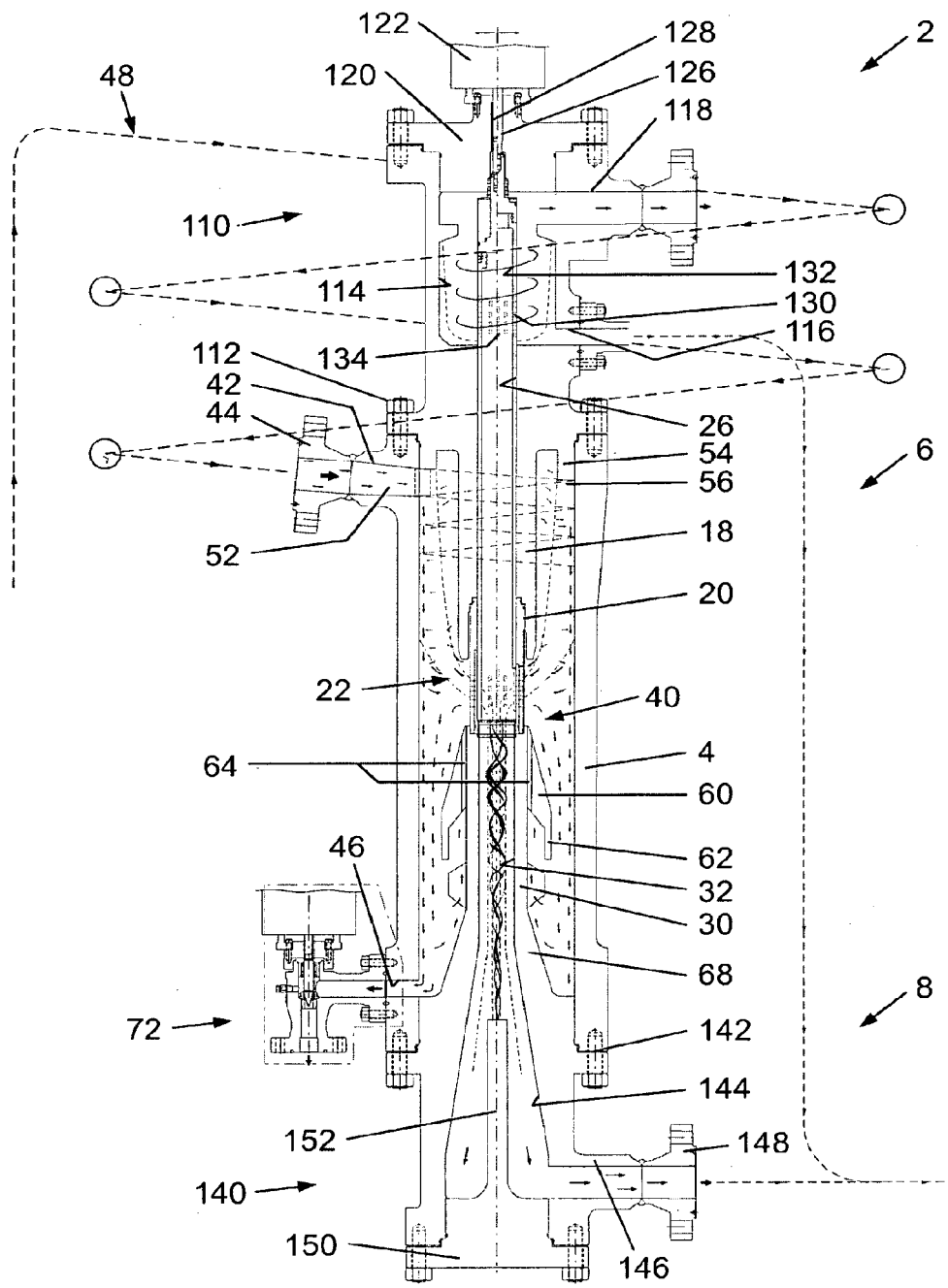
FIG. 6 is a cross-sectional view of a third embodiment of a choke assembly of the present invention.

Referring to FIG. 6, there is shown a further embodiment of a choke assembly according to the present invention. The choke assembly of FIG. 6 has the same general arrangement and configuration as that of FIGS. 1 and 5 and the components and features common to both embodiments are indicated using the same reference numerals. The follow description will concentrate on the features of the choke assembly of FIG. 6 that are not shared with the assemblies of FIGS. 1 and 5.

The choke assembly 2 of FIG. 6 comprises a cap assembly 110, in place of the end cap 10 at the inlet end 6 of the assembly. The cap assembly 110 is secured to the housing 4 by means of bolts 112, in conventional manner. The cap assembly 110 comprises a central mandrel 18 extending coaxially into the housing 4 to support the choke element 22, as hereinbefore described. The cap assembly 110 comprises a gas/liquid separation chamber 114 formed as a generally cylindrical cavity in the cap. The separation chamber 114 has a first outlet 116 for liquid, the opening of which extends from through the cap at the end of the separation chamber 114 adjacent the housing 4. The first fluid outlet 116 terminates in a conventional flanged coupling and is arranged with an opening that is tangential to the separation chamber 114, so as to allow the efficient removal of liquid from a rotating fluid stream in the chamber. The separation chamber 114 has a second outlet 118 extending from the end of the chamber distal to the housing 4 and terminating in a conventional flanged coupling. Again, the second outlet 118 is arranged to have an opening that is tangential to the separation chamber 114. The cap assembly 110 comprises an end cap 120 mounted to the end of the cap assembly and closing the separation chamber 114. A choke actuator 122 of conventional design is mounted on the exterior of the end cap 120.

As described hereinbefore and shown in FIGS. 1 and 6, the mandrel 18 has a central longitudinal bore 26 in which is housed a stem 28. In the embodiment shown in FIG. 6, the bore 26 extends through the end cap assembly 110 and opens into the separation chamber 114. A further longitudinal bore 126 extends through the end cap 120. A stem 128 extends from the actuator 122 through the bore 126 in the end cap into the separation chamber 114. A stem conduit 130 is connected to the free end of the stem 128 within the separation chamber 114 and extends through the bore 26 in the cap assembly into the choke element 22. The end portion of the stem conduit 130 within the choke element 22 forms the plug of the choke element. The stem conduit 130 is generally cylindrical and has a longitudinal bore 132 extending therethrough along its entire length. The bore 132 in the stem conduit 130 is open at the end within the choke element 22 and provides an outlet for lighter fluid phases to leave the choke element in operation. The end portion of the stem conduit 130 extending into the separation chamber 114 in the cap assembly 110 is provided with a plurality of tangential openings 134, through which fluid may leave the stem conduit 130 and enter the separation chamber 114 in a rotating flow pattern.

The choke assembly 2 of FIG. 6 further comprises a cap assembly 140, in place of the end cap 14 at the outlet end 6 of the assembly. The cap assembly 140 is secured to the housing 4 by means of bolts 142, in conventional manner. The cap assembly 140 comprises a central mandrel 30 of the type shown in FIG. 5 and extending coaxially into the housing 4 to support the choke element 22, as hereinbefore described. The central mandrel has a longitudinal bore 32 extending therethrough. The cap assembly 140 further comprises a fluid collection chamber 144 formed by a tapered cavity extending longitudinally within the cap assembly 140 from the bore 32 in the mandrel 30. The cavity is tapered so as to widen in the downstream direction towards a fluid outlet 146 terminating in a conventional flange coupling 148. The fluid outlet 146 is arranged to have its opening extending tangentially from the collection chamber 144. An end cap 150 is mounted to the cap assembly 140 and closes the collection chamber 144. A cylindrical vortex breaker 152 extends from the end cap 150 coaxially within the collection chamber, terminating downstream of the bore 32 in the mandrel 30. The vortex breaker 152 serves to prevent a gas vortex extending from the choke element 22 downstream into the collection chamber 144.

Operation of the choke assembly of FIG. 6 will now be described, using as a reference example the aforementioned fluid stream.

Operation of the choke assembly upstream of the choke element 22 is as described hereinbefore with reference to FIGS. 1 to 5. Passing through the choke cage is a fluid stream comprising a major portion of gas and the lighter liquid phase, oil. Some minor amounts of heavier liquid, water, and solid material may be entrained in the lighter fluid stream. The choke element is arranged to generate a rotational fluid flow regime within the choke cage. The details of a choke element to achieve are described below. The rotational flow regime causes the liquid phase to migrate to the radially outer regions of the cavity within the choke element and the gas phase to collect in the central region. The gas flows from the choke element into the bore 132 in the stem conduit 130 and flows through the bore, exiting through the tangential openings 134 into the separation chamber 114. The arrangement of the tangential openings 134 causes the fluid in the separation chamber 114 to rotate and swirl. Liquid and heavier fluids, such as oil and minor quantities of water, entrained in the gas migrate to the radially outer region of the separation chamber 114 and pass to the outlet 116. Gas entering the separation chamber 114 collects in the central region and exits through the outlet 118.

Heavier fluid phases, in particular oil and minor quantities of water and entrained solids, leave the choke element and flow downstream along the bore 32 in the mandrel 30 to the collection chamber 144 in the cap assembly 140. The tendency of the rotating gas stream to vortex downstream into the collection chamber 144 is damped or inhibited by the vortex breaker 152. The liquid, still flowing in a rotating flow regime, leaves the collection chamber 144 through the outlet 146.

Figure 7:
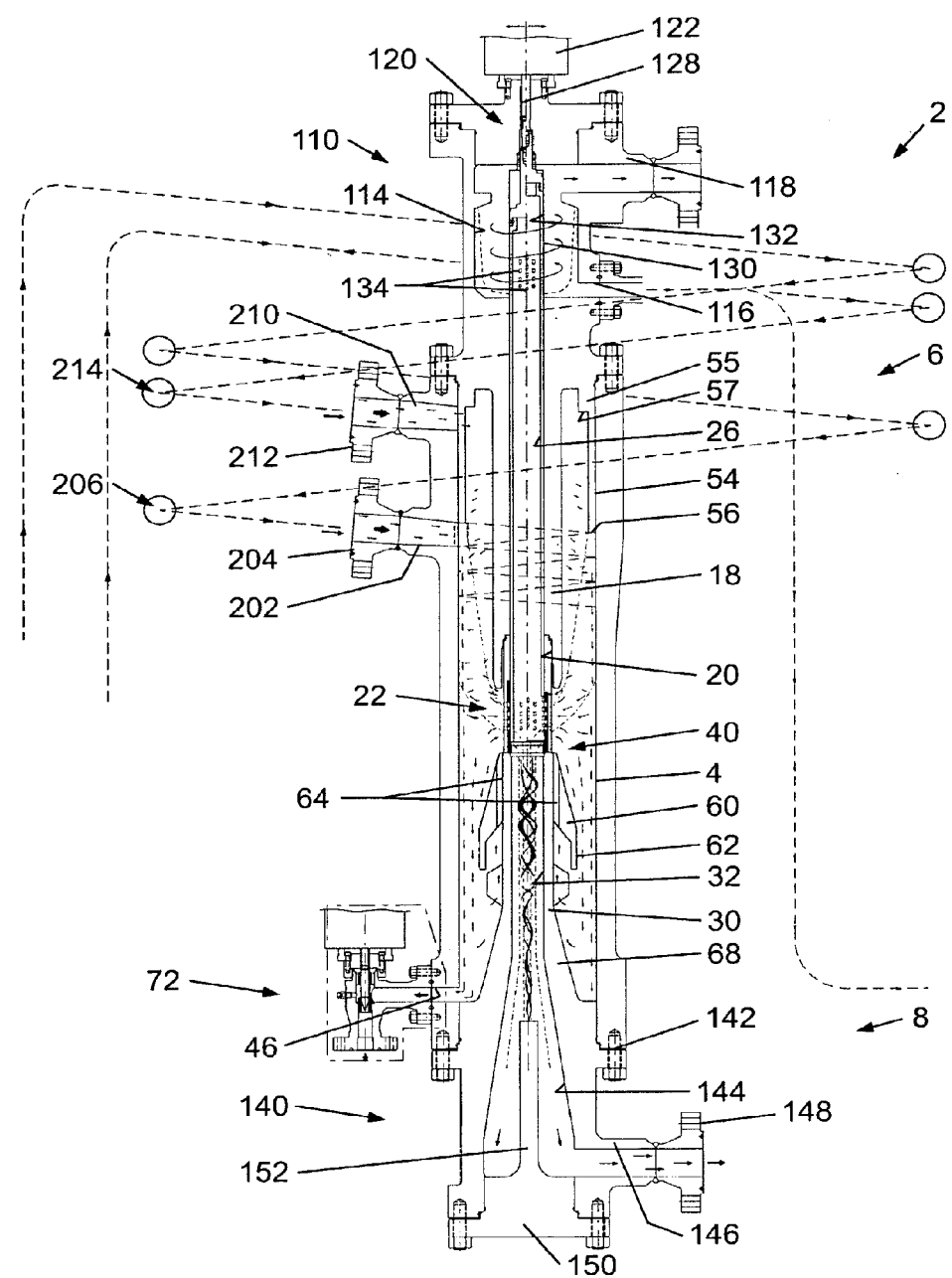
FIG. 7 is a cross-sectional view of a fourth embodiment of a choke assembly of the present invention.

Referring to FIG. 7, there is shown a further embodiment of a choke assembly according to the present invention. The choke assembly of FIG. 7 is of the same general configuration as that shown in FIG. 6 and described above. Features and components common to the assemblies of FIGS. 6 and 7 are indicated using the same reference numerals.

The choke assembly of FIG. 7 differs from that of FIG. 6 by comprising two fluid inlets for introducing fluid into the separation chamber 40. A first fluid inlet 202 is provided in the housing 4 and is disposed between the choke element 22 and the inlet end 6 of the housing. The first inlet 202 terminates in a conventional flange coupling 204. The inlet 202 is an angled, tangential inlet having the same arrangement and configuration as described above and shown in FIG. 3. An inlet assembly 206 is connected to the inlet 202 and has the general configuration described hereinbefore and shown in FIG. 2a. The inlet assembly serves to precondition the incoming fluid stream, as described above. The first fluid inlet is for a multiphase fluid stream, in particular a stream comprising multiple liquid phases and optionally suspended or entrained solid material.

A second fluid inlet 210 is provided in the housing 4 and is disposed between the first fluid inlet 202 and the inlet end 6 of the housing. The second inlet 210 terminates in a conventional flange coupling 212. The inlet 210 is an angled, tangential inlet having the same arrangement and configuration as described above and shown in FIG. 3. An inlet assembly 214 is connected to the inlet 210 and has the general configuration described hereinbefore and shown in FIG. 2a. The inlet assembly serves to precondition the incoming fluid stream, as described above. The second fluid inlet is for a multiphase fluid stream, in particular a stream comprising a major portion of gas with entrained liquid droplets or condensate.

Figure 8:
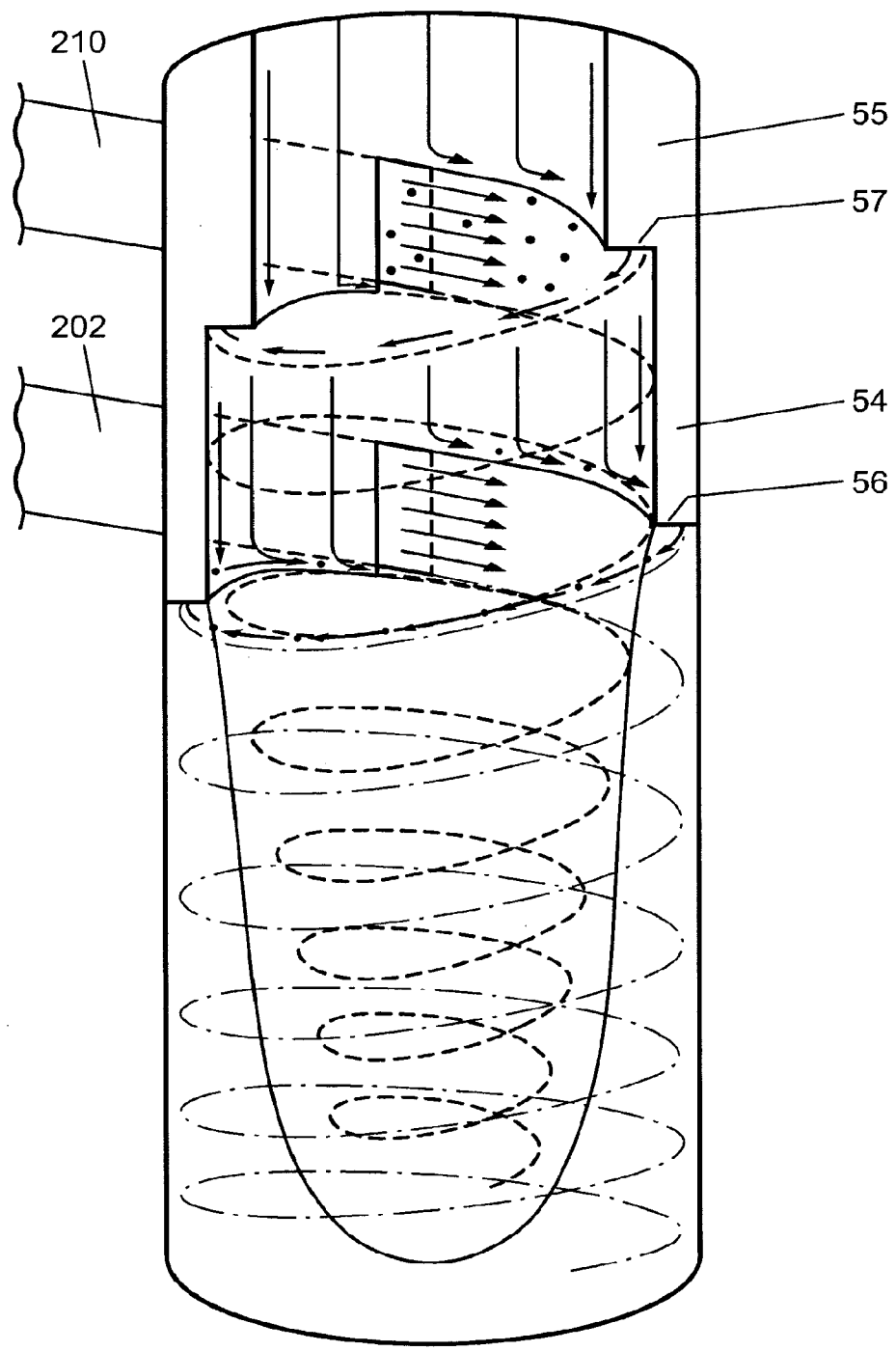
FIG. 8 is a representation of the fluid flow pattern within the separation chamber of the choke assembly of FIG. 7.

Overall, the operation of the assembly of FIG. 7 is as described above with reference to the choke assembly of FIG. 6. A multiphase fluid stream comprising a major portion of liquid phases is introduced via the first inlet 202 into the separation chamber and forms a helical flow regime below the projection 54, which presents a lower helical surface of a dual wall ramp 56 to the flow. A predominantly gas stream is introduced into the separation chamber 40 through the second inlet 210 directly into a gas cap formed within the separation chamber 40 upstream of the first inlet. A projection 55 presents an upper helical surface 57 of a dual wall ramp to the incoming fluid. The general flow pattern within the separation chamber 40 is represented in FIG. 8. As shown, a gas/liquid interface is established, with the liquid lining the outer wall of the separation chamber 40 and surrounding a gaseous core. Entrained liquid droplets in the gas stream entering through the second inlet 210 are captured in the liquid phase. Similarly, gas present in the liquid stream entering through the first inlet 202 is caused to leave the liquid phase and enter the gaseous core. The remainder of the operation is as hereinbefore described.

The choke assembly of FIG. 7 is particularly useful in the processing of large volumes of both gaseous and liquid streams, where it is required to remove entrained liquid from the gas and to release gases from the liquid stream.

Figure 9:
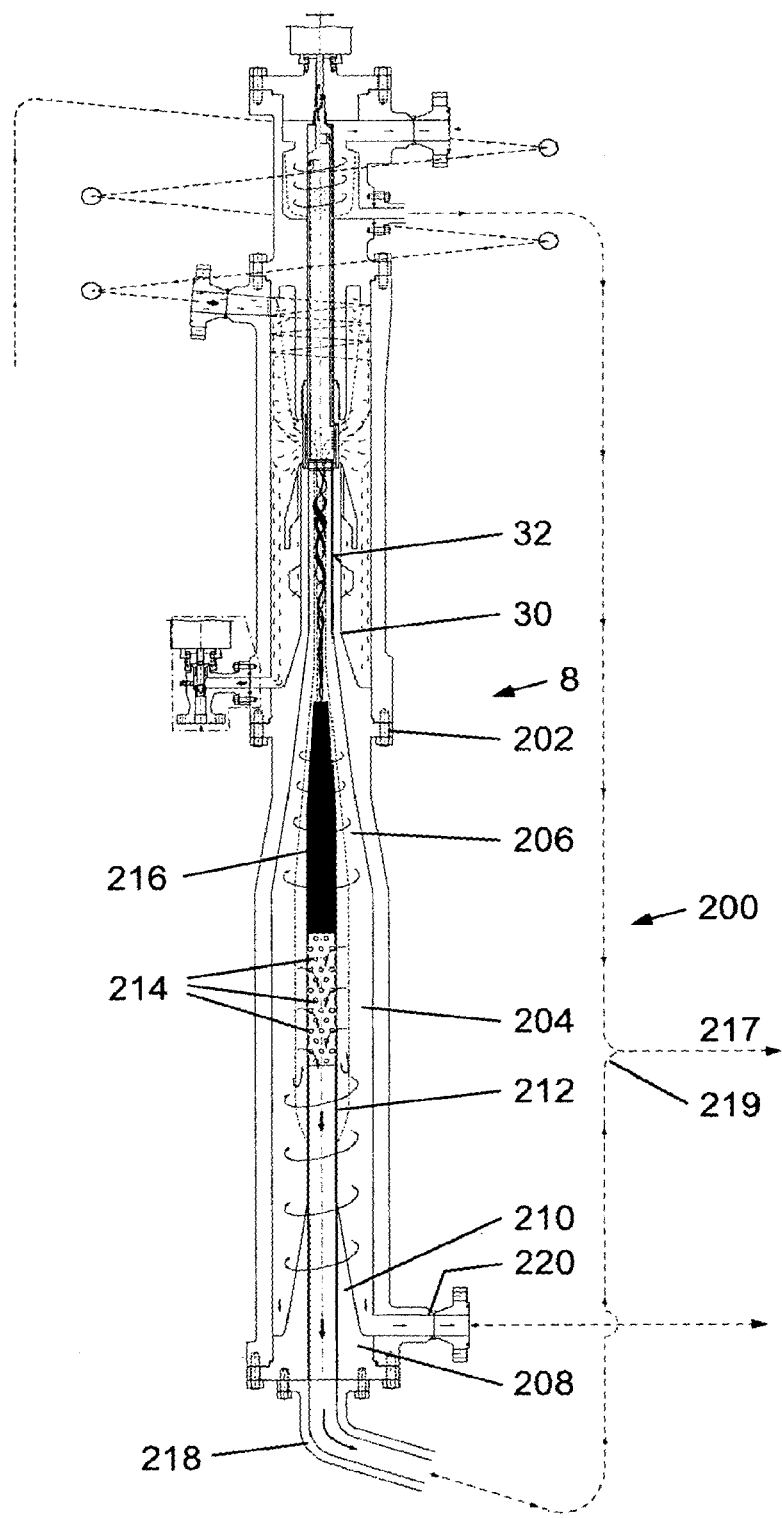
FIG. 9 is a cross-sectional view of a fifth embodiment of a choke assembly of the present invention.

Referring to FIG. 9, there is shown a further embodiment of a choke assembly according to the present invention. The choke assembly of FIG. 9 has the same general configuration to that shown in FIG. 6, with the exception of the end cap assembly 140, which is replaced by an end cap separation assembly 200, the details of which are as follows:

The end cap separation assembly 200 of the assembly of FIG. 9 is mounted to the outlet end 8 of the housing bolts in conventional manner. The end cap assembly has a mandrel 30 extending coaxially into the housing 4, with all the features described above and shown in FIG. 6. The bore 32 in the mandrel 30 opens into a liquid separation chamber 204. The liquid separation chamber 204 is generally cylindrical in shape, having a tapered section 206 adjacent the end of the bore 32 in the mandrel and widening in the downstream direction. The generally cylindrical separation chamber 204 is closed by an end cap 208, mounted to the end cap assembly 200 by bolts in conventional manner. The end cap 208 has a conical projection 210 extending into the separation chamber 204, to reduce the cross-sectional area of the separation chamber 204 in the region immediately upstream of the end cap 208. A cylindrical conduit 212 extends through a bore in the end cap 208 and coaxially into the separation chamber 204. The cylindrical conduit 212 is provided with a plurality of tangential openings 214, through which fluid from the separation chamber 204 can enter the conduit 212. The distal end of the conduit is closed and is capped by a vortex arrestor 216, extending coaxially within the separation chamber 204 towards the opening of the conduit 32 in the mandrel 30.

A first liquid outlet 218 is mounted to the exterior of the end cap 208 and provides a flowpath for fluid leaving the assembly. A second fluid outlet 220, terminating in a conventional flanged coupling, is provided in the end cap assembly 200 adjacent the end cap 210, for fluid leaving the separation chamber 204.

In operation, the choke assembly of FIG. 9 performs as described above with reference to FIG. 6 upstream of the bore 32 in the mandrel 30 extending from the end cap 140. In the choke assembly of FIG. 9, fluid, predominantly lighter liquid, in particular oil, with some entrained heavier liquid, that is water, flows downstream from the bore 32 in the mandrel 30 and enters the upstream end of the separation chamber 204 in the end cap separation assembly 200. The tendency of gas from the choke element 22 to form a vortex down into the separation chamber 204 is prevented by the vortex breaker 216, resulting in a substantially liquid stream flowing through the separation chamber 204. The liquid stream is rotating, under the action of the choke element, as will be described hereinafter. The action of the rotation is to cause the heavier liquid phase, water, to migrate to the outer wall of the separation chamber 204 and for the lighter liquid phase, oil, to concentrate in the radially central region. Oil gathered in this central region passes through the tangential openings 214 in the conduit 212 and flows downstream through the end cap 208 to the first outlet 218. The oil takes an upwards flowpath over a level weir 219, before exiting through an outlet 217. Water, the heavier liquid phase, remains in the separation chamber 204 and flows downstream to the second outlet 220 in the end cap assembly.

Figure 10:
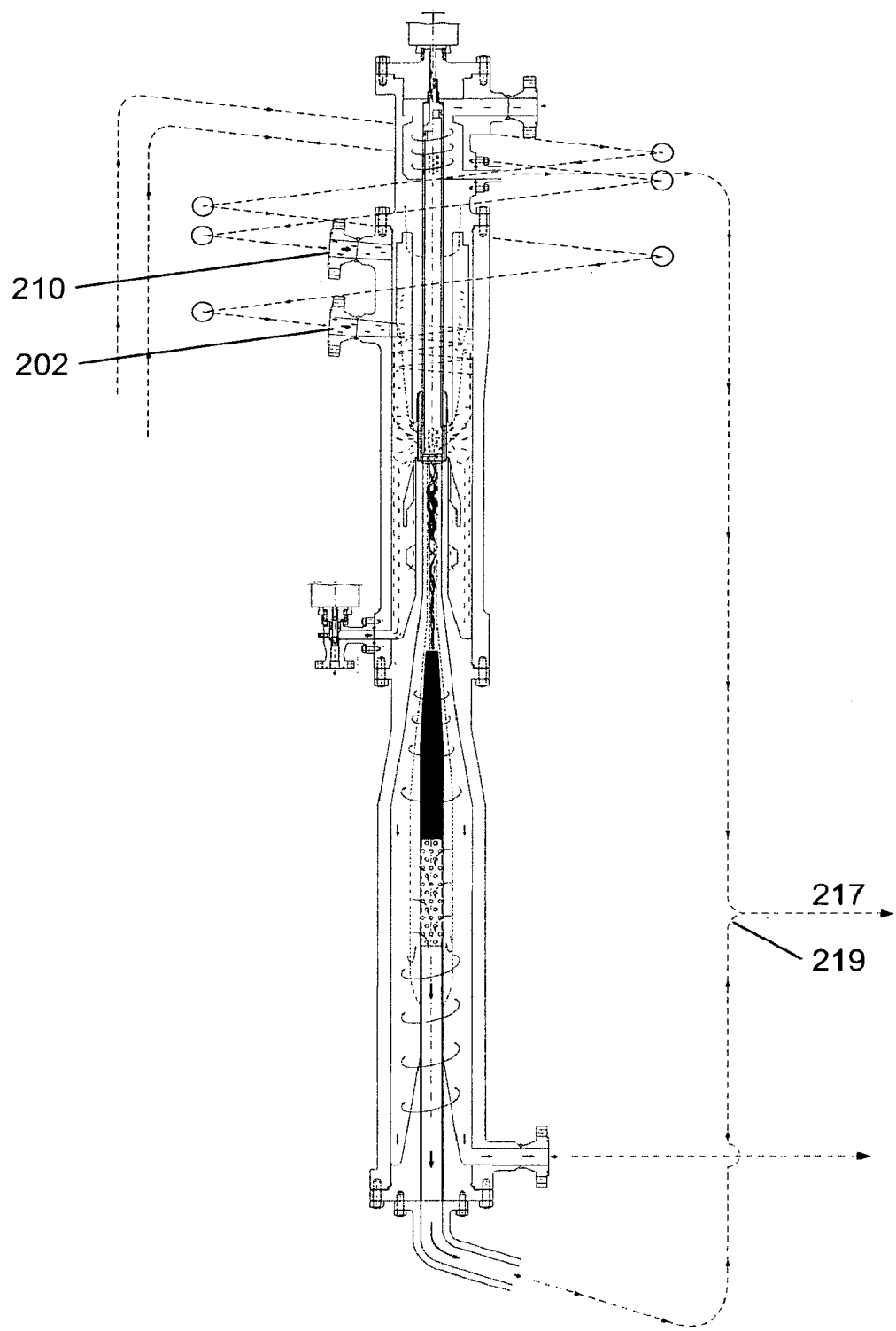
FIG. 10 is a cross-sectional view of a sixth embodiment of a choke assembly of the present invention.

Referring to FIG. 10, there is shown an alternative embodiment of the choke assembly of FIG. 9, having two fluid inlets, as shown in FIG. 7 and described hereinbefore.

As noted above, a preferred choke element for use in the choke assemblies of the present invention is one in which the fluid passing through the choke element is caused to flow in a rotational flow regime within the choke element. As noted above, this rotational flow of fluid allows for various separation stages to take place, enhancing the processing of multiphase fluid streams using the choke assembly. A preferred arrangement of choke element is shown in FIG. 11 and will now be described.

Referring to FIG. 11, there is shown a choke element, generally indicated as 300, in place in the choke assembly of FIG. 1. It will be understood that the choke assembly 300 is not limited in its use to the choke assembly of FIG. 1 and can equally well be applied in the choke assemblies of other embodiments of the present invention, as well as choke assemblies falling outside the scope of the invention. The left hand side of FIG. 11 shows the choke element in the fully closed position, while the right hand side of the figure shows the choke element in the fully open position.

The choke element 300 is of the plug and cage variety and comprises a generally cylindrical cage 302 having an inner cage portion 304 and an outer cage portion 306 arranged concentrically. The outer cage portion 306 is supported between the mandrel 18 extending from the end cap at the inlet end within the recess 20 in the end of the mandrel 18 and the mandrel 30 extending from the end cap at the outlet end. The choke element 300 further comprises a generally cylindrical plug 308 disposed within the cage 302. The plug 308 is connected in conventional manner to the end of the stem 28 extending from the actuator mounted to the end cap at the inlet end of the housing. In this manner, the plug 308 may be moved longitudinally within the cage by a reciprocating motion of the stem 28 under the action of the actuator.

As noted, the choke element 300 shown in FIG. 11 has the plug disposed within the cage. It will be understood that the present invention embraces a similar choke element, but in which the plug is disposed outside the cage. To achieve a 'shut-off' that is complete closure of the choke assembly, the plug has a seat 309 which seals on a cage shoulder 307.

Figure 12:
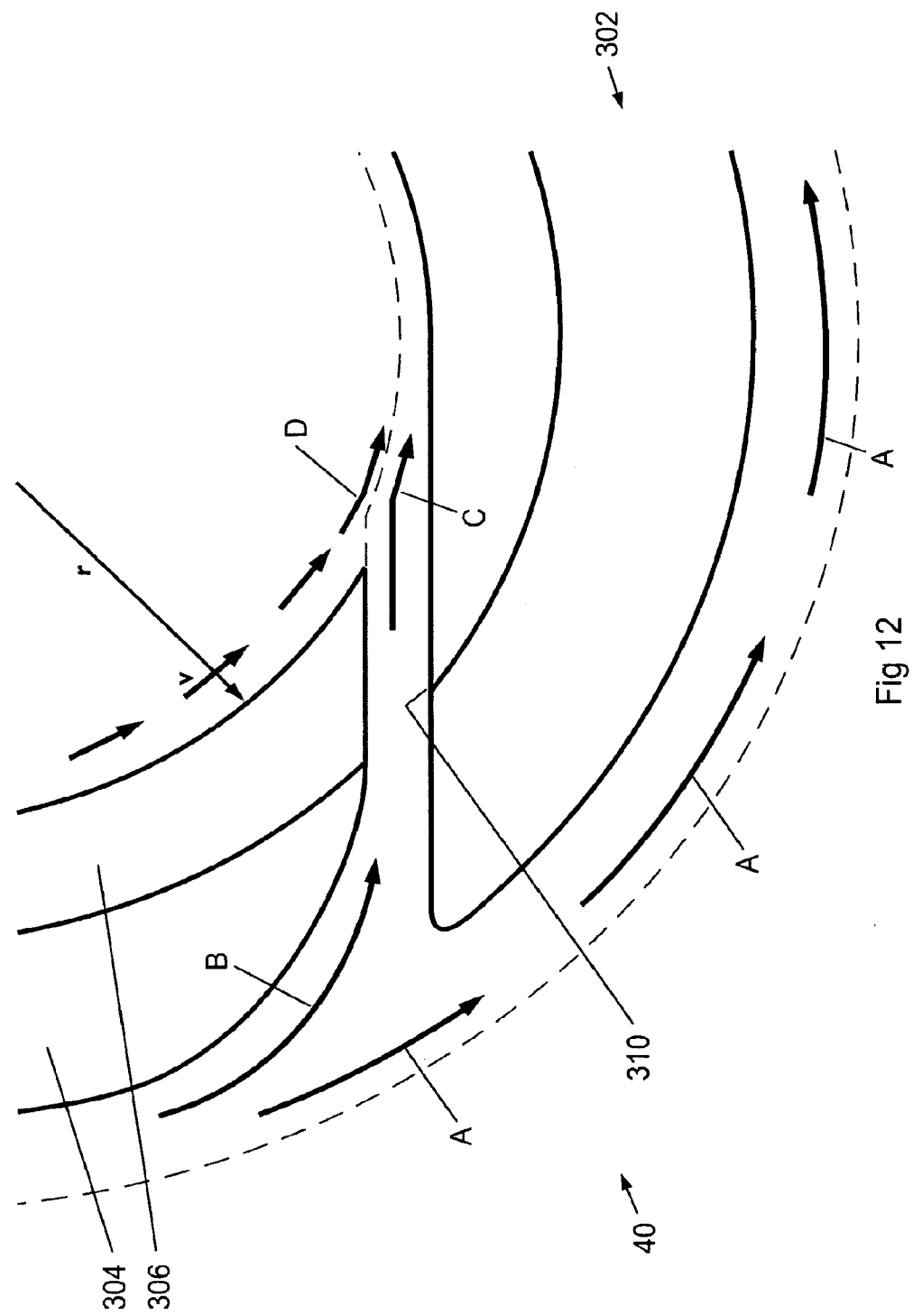
FIG. 12 is a cross-sectional view of a portion of the choke cage of the choke element of FIG. 11 showing a detail of the opening therethrough.

The cage 302 is provided with a plurality of openings 310, through which fluid may flow from the separation chamber 40 into the central cavity within the choke element 300. The openings 310 are formed to extend tangentially through the cage 302. Referring to FIG. 12, there is shown a cross-sectional view through a portion of the choke cage 302 showing the form of an opening 310. Each opening 310 extends through both the outer cage portion 304 and the inner cage portion 306. The openings are generally rectangular in cross-section. The portion of each opening extending through the inner cage portion 306 has a constant cross-sectional area throughout its length. The portion of each opening extending through the outer cage portion 304 is tapered, with the cross-sectional area of the opening at the outer surface of the outer cage portion being widest, the opening tapering in a radially inwards direction such that the cross-sectional area reduces to that of the opening portion in the inner cage portion. As shown in FIG. 12, the taper of the opening portion in the outer cage portion 304 is not symmetrical, but rather is offset in the reverse direction of fluid flow around the outside of the cage, as indicated by arrows A.

The inner cage portion 306 is formed from tungsten, with the exposed openings acting as the fluid throttling means. The outer cage portion 304 is formed from stainless steel. Tungsten is a very hard material, resistant to erosion. However, tungsten is a brittle material and is easily fractured upon impact by solid material. Accordingly, the outer cage portion 306, being of stainless steel, while less resistant to erosion, is less brittle than the tungsten inner portion and better able to resist fracturing under impact.

The fluid flow patterns in and around the cage 302 are shown in FIG. 12. Fluid in the separation chamber 40 is flowing in a rotating pattern around the exterior of the cage 302, as indicated by arrows A. As the fluid passes the outer end of an opening 310, a portion of the fluid is directed into the opening, as indicated by arrow B. The offset in the taper in the outer portion of the opening reduces the shear experienced by the fluid as it enters the opening 310. As the fluid passes through the opening, the reduction in cross-sectional area accelerates the fluid velocity, such that upon entering the inner cavity of the choke element, the fluid is travelling at a high velocity. The angle of the opening 310 introduces the high velocity fluid into the inner cavity tangentially, as indicated by arrow C. As a result of the tangential entry, the fluid within the inner cavity is caused to rotate, as shown by arrows D. Thus, the incoming fluid indicated by arrow C is caused to change direction, as shown in FIG. 12, and follow a flow path close to the inner surface of the inner cage portion 306. Overall, this pattern of flow reduces the degree of shear to which the fluid is subjected, which in turn has the effect of maintaining phase separation that exists in the fluid prior to entering the cage. In addition, as will be appreciated, any solid particles entrained in the fluid are caused to take a circular path within the choke cage 302, rather than impact equal and opposite fluid jets within the cage, as with choke assemblies of conventional design. This significantly reduces fluid shear, erosion of the cage and failure rates of the choke element.

As shown in FIG. 11, the openings in the choke cage 302 are arranged in bands. Cross-sectional views through the six downstream bands of the choke cage 302 are shown in FIGS. 13a to 13f. The most downstream band is shown in FIG. 13a and has two openings 310 arranged at 180° to each other on opposing sides of the cage 302. Similarly, the adjacent upstream band, shown in FIG. 13b, has two openings arranged at 180° to each other on opposing sides of the cage, but offset by 90° to the openings in the band shown in FIG.

13a. The adjacent upstream band is shown in FIG. 13c and has four openings arranged at 90° to each other around the cage. The band immediately upstream is shown in FIG. 13d, which also comprises four openings with a 90° spacing, again offset from the four openings of the adjacent downstream band by 45°. The upstream pair of bands is shown in FIGS. 13e and 13f, each band having eight openings.

Movement of the plug 308 longitudinally within the cage 302 allows the bands of openings to be covered and uncovered, depending upon the position of the plug, thereby allowing the flow of fluid through the choke element to be controlled. With the plug in the position shown in the left hand side of FIG. 11, all bands of openings are covered and the choke element is closed to fluid flow. Movement of the plug 308 from the closed position first uncovers the band shown in FIG. 13a and then, successively, the bands of FIGS. 13b to 13f, until the fully open position shown in the right hand side of FIG. 11 is reached. It will be appreciated that movement of the plug from the closed position to the open position opens bands having successively a greater number of openings and, hence, providing a successively increasing cross-sectional area available for fluid flow.

Figure 14A:
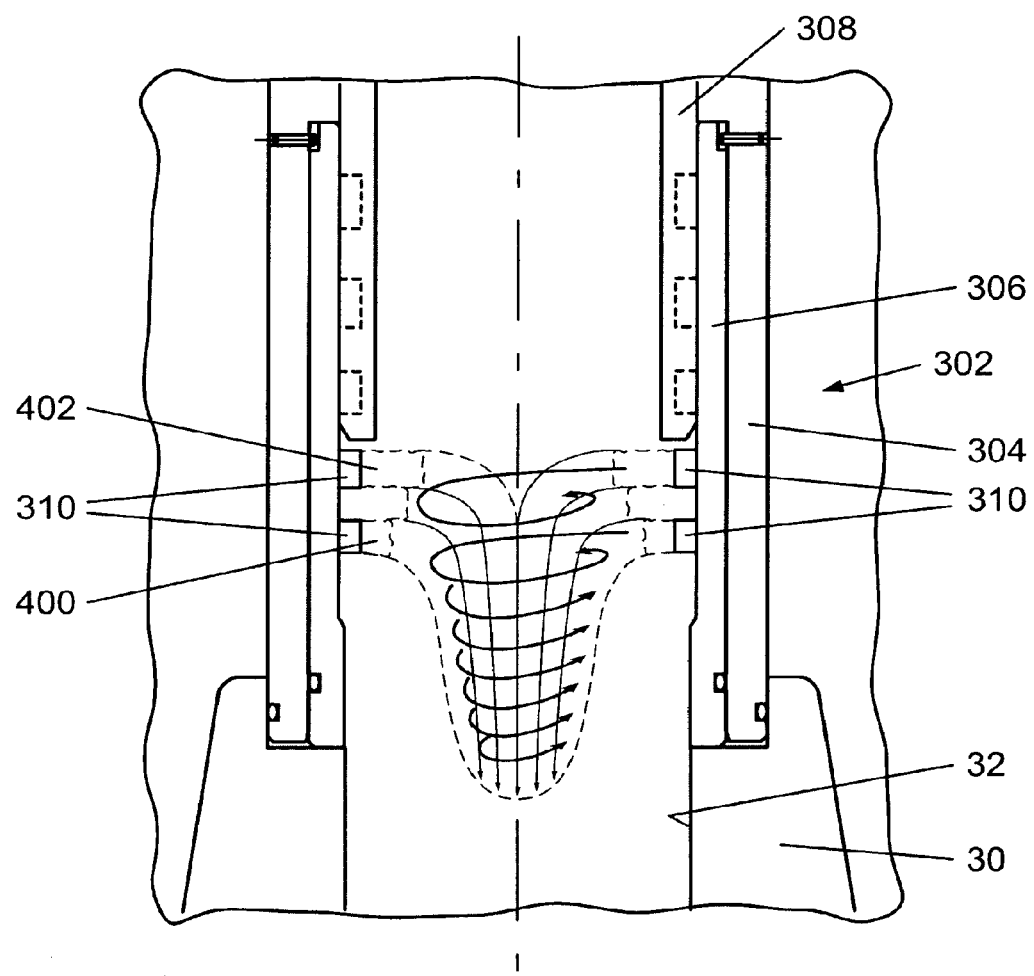
FIGS. 14a and 14b are diagrammatic representations of fluid flow patterns during the operation of the choke assembly of FIG. 11.
Figure 14B:
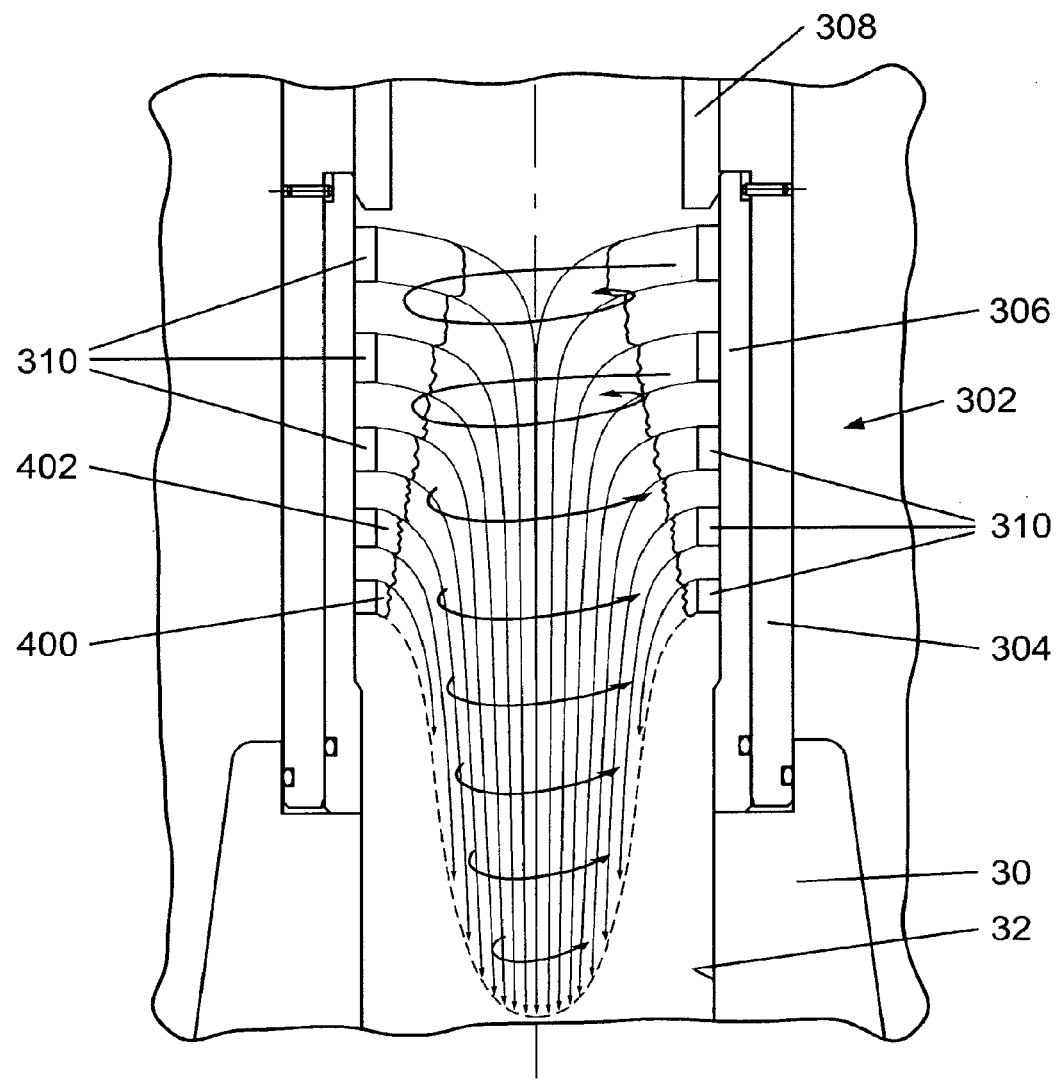

It has been found that the arrangement of the tangential openings 310 into bands, as described hereinbefore, induces a particular flow regime, represented in FIGS. 14a and 14b. As described hereinbefore and shown in FIG. 12, the fluid entering the cavity within the cage element is caused to flow in a circular path adjacent the inner surface of the inner cage portion 306, that is form a rotating band of pressurised fluid in the radially outer region of the cavity. The pressurised centrifugal band of fluid 400 generated by the downstream band of openings is shown in FIGS. 14a and 14b. The general direction of fluid flow within the choke element is downstream towards the bore 32 in the mandrel 30 (that is downwards, as shown in FIGS. 14a and 14b). However, the effect of the pressurised centrifugal band 400 is to reduce the effective cross-sectional area available for the flow of fluid entering the choke element upstream of the band 400. In other words, the pressurised centrifugal band of fluid acts as a hydraulic choke to the flow of fluid downstream. A similar pressurised centrifugal band of rotating fluid 402 will be formed by the adjacent upstream band of openings, which acts to further reduce the effective cross-sectional area available for the downstream flow of fluid.

As shown in FIG. 14a, the choke element is in the partially open position, with the plug 308 in an intermediate position between the fully open and fully closed positions and two bands of openings uncovered for fluid flow. The effect of the hydraulic choke action within the choke cavity is represented. In FIG. 14b, the plug 308 is in the fully open position, with all bands of openings uncovered. The hydraulic choke action of successive fluid bands is shown. The fluid entering the cavity through a given band of openings must flow in the general downstream direction. To do this, the fluid is caused to flow inwards, past the pressurised centrifugal band of fluid established by the fluid entering the adjacent downstream band of openings. As shown in FIG. 14b, the cumulative effect of the pressurised centrifugal bands of fluid results in the fluid entering the choke cavity through the most upstream bands of openings having a very limited cross-sectional area available for flow past the downstream fluids bands.

The hydraulic choke action of the pressurised centrifugal fluid bands acts in addition to the physical choking action provided by the flow of fluid through the openings in the choke cage. Thus, the choke employs three different mechanisms for choking the flow of fluid: the mechanical choking effect provided by the fluid flowing through restricted orifices (as with conventional choke designs); the hydraulic choking effect caused by the rotating bands of fluid within the choke cage providing resistance to the entry of fluid into the cage; and the hydraulic choking effect of the bands of fluid creating hydraulic orifices (as shown in FIGS. 14a and 14b) providing resistance to the general fluid flow within the cage. The hydraulic choke action can be employed to control the flow of fluid downstream of the choke element, but has the advantage of subjecting the fluid to significantly less shear than the components of the choke element, such as would be experienced in a conventional plug and cage choke assembly.

What is claimed is:

1. A choke assembly for controlling flow of a multiphase fluid stream including a relatively heavy fluid phase and a relatively light fluid phase, including:
    a separation chamber to provide separation of the fluid stream phases;
    a chamber outlet in fluid communication with the separation chamber;
    a choke element in fluid communication with the separation chamber to receive one of the separated fluid phases; and
    a choke outlet in fluid communication with the choke element.

2. The choke assembly of claim 1, wherein the choke element is adjustable to control at least one of flowrate and fluid pressure of the multiphase fluid stream flowing through the assembly.

3. The choke assembly of claim 1, wherein the choke element is disposed in the separation chamber.

4. The choke assembly of claim 1, wherein the choke element is arranged concentrically in the separation chamber.

5. The choke assembly of claim 1, wherein the separation chamber extends around the choke element.

6. The choke assembly of claim 1, wherein the choke element comprises a flowpath for the separated relatively light fluid phase.

7. The choke assembly of claim 1, wherein the separation chamber and choke element are positioned such that in operation the multiphase fluid is separated before the fluid passes through the choke element.

8. The choke assembly of claim 1, further comprising an inlet disposed to direct the multiphase fluid stream into the separation chamber upstream of the choke element.

9. The choke assembly of claim 8, wherein the inlet is angled to direct the multiphase fluid into the separation chamber at an angle to the normal of a longitudinal axis of the separation chamber.

10. The choke assembly of claim 8, further including more than one inlet.

11. The choke assembly of claim 1, further including an inlet assembly in fluid communication with the separation chamber and including a curved flow path such that in operation, separation of the fluid phases begins to occur prior to the fluid entering the separation chamber.

12. The choke assembly of claim 1, wherein a region of the separation chamber downstream of the choke element, in operation allows gravity-assisted separation of solid particles in the fluid stream.

13. The choke assembly of claim 1, further including a means to reduce or prevent fluid rotation within the upstream region adjacent the separation chamber outlet.

14. The choke assembly of claim 1, further including a means for separating fluid phases that leave the separation chamber through the choke element.

15. The choke assembly of claim 1, further including a cap separation chamber to provide separation of the fluid stream phases including:
- an inlet to receive fluid from the choke element;
- a first cap outlet for a first separated fluid phase; and
- a second cap outlet for a second separated fluid phase, the second cap outlet being in fluid communication with the separation chamber for introduction of the second separated fluid phase into the separation chamber.

16. The choke assembly of claim 1, further including an end cap separation assembly including:
- a liquid separation chamber in fluid communication with the choke outlet to provide separation of phases of the fluid from the choke;
- a vortex breaker in the separation chamber to inhibit or prevent the formation of a vortex in the separation chamber; and
- a conduit extending within the separation chamber and including tangential openings in fluid communication with the separation chamber.

17. The choke assembly of claim 16, further comprising a liquid separation chamber outlet and a conduit outlet.

18. The choke assembly of claim 16, further comprising more than one inlet disposed to direct the multiphase fluid stream into the separation chamber upstream of the choke element.

19. The choke assembly of claim 1, wherein the choke element includes a plug disposed within a cage.

20. The choke assembly of claim 1, wherein the cage includes openings arranged in a plurality of bands extending circumferentially around the cage.

* * * * *